(12) United States Patent　　(10) Patent No.:　US 9,005,550 B2
Carter et al.　　(45) Date of Patent:　Apr. 14, 2015

(54) MULTI-LAYERED CELL CULTURE VESSEL WITH MANIFOLD GRIPS

(71) Applicant: Corning Incorporated, Corning, NY (US)

(72) Inventors: Thomas L. Carter, Cary, NC (US); Gregory S. Jordan, Raleigh, NC (US)

(73) Assignee: Corning Incorporated, Corning, NY (US)

( * ) Notice: Subject to any disclaimer, the term of this patent is extended or adjusted under 35 U.S.C. 154(b) by 92 days.

(21) Appl. No.: 13/838,962

(22) Filed: Mar. 15, 2013

(65) Prior Publication Data

US 2014/0120608 A1　　May 1, 2014

Related U.S. Application Data

(60) Provisional application No. 61/719,593, filed on Oct. 29, 2012.

(51) Int. Cl.
*C12M 1/00*　　(2006.01)
*C12M 3/00*　　(2006.01)
*C12M 1/12*　　(2006.01)

(52) U.S. Cl.
CPC ............... *C12M 23/40* (2013.01); *C12M 3/00* (2013.01); *C12M 23/04* (2013.01)

(58) Field of Classification Search
None
See application file for complete search history.

(56) References Cited

U.S. PATENT DOCUMENTS

| 3,717,259 A * | 2/1973 | Fried et al. ............ 211/126.9 |
| 3,821,087 A | 6/1974 | Knazek et al. |
| 3,948,732 A | 4/1976 | Haddad et al. |
| 3,997,396 A | 12/1976 | Delente |
| 4,172,013 A | 10/1979 | Skoda et al. |
| 4,184,916 A | 1/1980 | Tolbert et al. |
| 4,225,671 A | 9/1980 | Puchinger et al. |
| 4,332,906 A | 6/1982 | Taylor |
| 4,391,912 A | 7/1983 | Yoshida et al. |
| 4,440,853 A | 4/1984 | Michaels et al. |
| 4,537,860 A | 8/1985 | Tolbert et al. |
| 4,647,539 A | 3/1987 | Bach |
| 4,649,114 A | 3/1987 | Miltenburger et al. |
| 4,661,458 A | 4/1987 | Berry et al. |
| 4,720,462 A | 1/1988 | Rosenson |
| 4,722,902 A | 2/1988 | Harm et al. |
| 4,734,373 A | 3/1988 | Bartal |
| 4,748,124 A | 5/1988 | Vogler |
| 4,749,654 A | 6/1988 | Karrer et al. |
| 4,804,628 A | 2/1989 | Cracauer et al. |
| 4,874,707 A | 10/1989 | Bock |
| 4,889,812 A | 12/1989 | Guinn et al. |
| 4,897,359 A | 1/1990 | Oakley et al. |

(Continued)

FOREIGN PATENT DOCUMENTS

DE　　83 09 876 U1　　12/1983
EP　　1 514 919 A1　　3/2005

(Continued)

*Primary Examiner* — Jill Warden
*Assistant Examiner* — Timothy G Kingan
(74) *Attorney, Agent, or Firm* — Hoffmann & Baron, LLP

(57) ABSTRACT

The disclosure provides a multi-layered cell culture vessel having a rectangular shape with a top a bottom sides and ends, where the sides are longer than the ends. The vessel has hand grips and ports at each end of the rectangular vessel. The ports allow fluid entering into the vessel to flow into the multiple cell culture layers through a manifold. The ports may be incorporated into the hand grips.

19 Claims, 20 Drawing Sheets

(56) References Cited

U.S. PATENT DOCUMENTS

| | | |
|---|---|---|
| 4,948,728 A | 8/1990 | Stephanopoulos et al. |
| 5,002,890 A | 3/1991 | Morrison |
| 5,015,585 A | 5/1991 | Robinson |
| 5,032,524 A | 7/1991 | Buntemeyer et al. |
| 5,064,764 A | 11/1991 | Besnainon et al. |
| 5,081,035 A | 1/1992 | Halberstadt et al. |
| 5,126,269 A | 6/1992 | Fike et al. |
| 5,135,853 A | 8/1992 | Dziewulski et al. |
| 5,149,649 A | 9/1992 | Miyamori et al. |
| 5,188,962 A | 2/1993 | Hasegawa et al. |
| 5,202,254 A | 4/1993 | Amiot et al. |
| 5,240,854 A | 8/1993 | Berry et al. |
| 5,268,298 A | 12/1993 | Fike et al. |
| 5,290,700 A | 3/1994 | Binot et al. |
| 5,310,676 A | 5/1994 | Johansson et al. |
| 5,316,945 A | 5/1994 | Minuth |
| 5,330,908 A | 7/1994 | Spaulding |
| 5,358,872 A | 10/1994 | Mussi et al. |
| 5,416,022 A | 5/1995 | Amiot |
| 5,437,998 A | 8/1995 | Schwarz et al. |
| 5,449,617 A | 9/1995 | Falkenberg et al. |
| 5,508,174 A | 4/1996 | DelRaso |
| 5,516,691 A | 5/1996 | Gerlach |
| 5,520,302 A * | 5/1996 | Anderson et al. ............. 220/800 |
| 5,523,235 A | 6/1996 | Barditch et al. |
| 5,576,211 A | 11/1996 | Falkenberg et al. |
| 5,602,028 A | 2/1997 | Minchinton |
| 5,622,857 A | 4/1997 | Goffe |
| 5,627,070 A | 5/1997 | Gruenberg |
| 5,656,494 A | 8/1997 | Kant et al. |
| 5,658,797 A | 8/1997 | Bader |
| 5,665,398 A | 9/1997 | McCormick |
| 5,686,301 A | 11/1997 | Falkenberg et al. |
| 5,702,945 A | 12/1997 | Nagels et al. |
| 5,705,390 A | 1/1998 | Kadouri et al. |
| 5,712,154 A | 1/1998 | Mullon et al. |
| 5,728,577 A | 3/1998 | Kuriyama |
| 5,763,261 A | 6/1998 | Gruenberg |
| 5,856,176 A * | 1/1999 | Mathus et al. ............. 435/288.3 |
| 5,955,353 A | 9/1999 | Amiot |
| 5,981,211 A | 11/1999 | Hu et al. |
| 6,027,938 A * | 2/2000 | Barnes et al. ................. 435/392 |
| 6,107,085 A | 8/2000 | Coughlin et al. |
| 6,127,141 A | 10/2000 | Kopf |
| 6,214,574 B1 | 4/2001 | Kopf |
| 6,228,607 B1 | 5/2001 | Kersten et al. |
| 6,284,531 B1 | 9/2001 | Zhu |
| 6,342,388 B1 | 1/2002 | Van Den Wildenberg |
| 6,403,369 B1 | 6/2002 | Wood |
| 6,453,310 B1 | 9/2002 | Zander |
| 6,455,007 B1 | 9/2002 | Mansky et al. |
| 6,455,310 B1 | 9/2002 | Barbera-Guillem |
| 6,544,788 B2 | 4/2003 | Singh |
| 6,566,126 B2 | 5/2003 | Cadwell |
| 6,569,675 B2 | 5/2003 | Wall et al. |
| 6,593,136 B1 | 7/2003 | Geiss |
| 6,620,614 B1 | 9/2003 | Luth et al. |
| 6,642,019 B1 | 11/2003 | Anderson et al. |
| 6,670,713 B2 | 12/2003 | Gonzalez et al. |
| 6,702,178 B2 | 3/2004 | Bowers et al. |
| 6,794,184 B1 | 9/2004 | Mohr et al. |
| 6,855,542 B2 | 2/2005 | DiMilla et al. |
| 6,878,344 B2 | 4/2005 | Mansky et al. |
| 6,918,738 B2 | 7/2005 | Lafferty et al. |
| 6,933,144 B2 | 8/2005 | Cadwell |
| 6,987,019 B1 | 1/2006 | Rogalsky |
| 7,022,518 B1 | 4/2006 | Feye |
| 7,033,823 B2 | 4/2006 | Chang |
| 7,078,228 B2 | 7/2006 | Lacey et al. |
| 7,144,727 B2 | 12/2006 | Akers et al. |
| 7,179,636 B2 | 2/2007 | Guillot et al. |
| 7,229,820 B2 | 6/2007 | Wilson |
| 7,425,440 B2 | 9/2008 | Malinge et al. |
| 7,745,209 B2 | 6/2010 | Martin et al. |
| 7,745,210 B2 | 6/2010 | Martin |
| 7,820,431 B2 | 10/2010 | Kenney et al. |
| 7,867,761 B2 | 1/2011 | Esser et al. |
| 7,897,379 B2 | 3/2011 | Kenney et al. |
| 7,964,392 B2 | 6/2011 | Hatano et al. |
| 8,039,252 B2 | 10/2011 | Berry |
| 2001/0055803 A1 | 12/2001 | Wall et al. |
| 2003/0054544 A1 | 3/2003 | Gruenberg |
| 2003/0186428 A1 | 10/2003 | Guillot et al. |
| 2004/0029265 A1 | 2/2004 | Doi et al. |
| 2004/0043481 A1 | 3/2004 | Wilson |
| 2004/0132175 A1 | 7/2004 | Vetillard et al. |
| 2004/0152149 A1 | 8/2004 | Reid et al. |
| 2004/0203147 A1 | 10/2004 | Triffitt et al. |
| 2005/0101009 A1 | 5/2005 | Wilson et al. |
| 2005/0106717 A1 | 5/2005 | Wilson et al. |
| 2005/0239198 A1 | 10/2005 | Kunas et al. |
| 2006/0205065 A1 | 9/2006 | Bossi et al. |
| 2007/0026516 A1 | 2/2007 | Martin et al. |
| 2007/0031963 A1 | 2/2007 | Chang et al. |
| 2007/0065933 A1 | 3/2007 | Esser et al. |
| 2007/0254356 A1 | 11/2007 | Wilson et al. |
| 2008/0003671 A1 | 1/2008 | Martin |
| 2008/0118974 A1 | 5/2008 | Martin et al. |
| 2008/0176318 A1 | 7/2008 | Wilson et al. |
| 2008/0229649 A1 | 7/2008 | Wilson |
| 2008/0299649 A1 | 12/2008 | Martin et al. |
| 2009/0191620 A1 | 7/2009 | Martin et al. |
| 2009/0298163 A1 | 12/2009 | Bennett et al. |
| 2009/0298164 A1 | 12/2009 | Cattadoris et al. |
| 2010/0129900 A1 | 5/2010 | Clark et al. |
| 2010/0233797 A1 | 9/2010 | Daly |
| 2010/0273251 A1 | 10/2010 | Rhoads et al. |
| 2010/0304472 A1 | 12/2010 | Kim et al. |
| 2011/0258915 A1 | 10/2011 | Subhadra |
| 2011/0287541 A1 | 11/2011 | Cuello et al. |

FOREIGN PATENT DOCUMENTS

| | | |
|---|---|---|
| GB | 1 539 263 | 1/1979 |
| GB | 2 268 187 A | 1/1994 |
| WO | 9310211 | 5/1993 |
| WO | 9902646 | 1/1999 |
| WO | 2004076609 A1 | 9/2004 |
| WO | 2005035728 A2 | 4/2005 |
| WO | 2005044972 A2 | 5/2005 |
| WO | 2005047453 A1 | 5/2005 |
| WO | 2005066328 A1 | 7/2005 |
| WO | 2006099127 A1 | 9/2006 |
| WO | 2007015770 A1 | 2/2007 |
| WO | 2008069902 A2 | 6/2008 |
| WO | 2008073313 A2 | 6/2008 |
| WO | 2008073314 A2 | 6/2008 |
| WO | 2008106012 A1 | 9/2008 |
| WO | 2008153783 A1 | 12/2008 |
| WO | 2009094125 A1 | 7/2009 |
| WO | 2009136907 A1 | 11/2009 |
| WO | 2009148512 A2 | 12/2009 |
| WO | 2010006055 A2 | 1/2010 |
| WO | 2010008566 A2 | 1/2010 |
| WO | 2010099264 A2 | 9/2010 |

\* cited by examiner

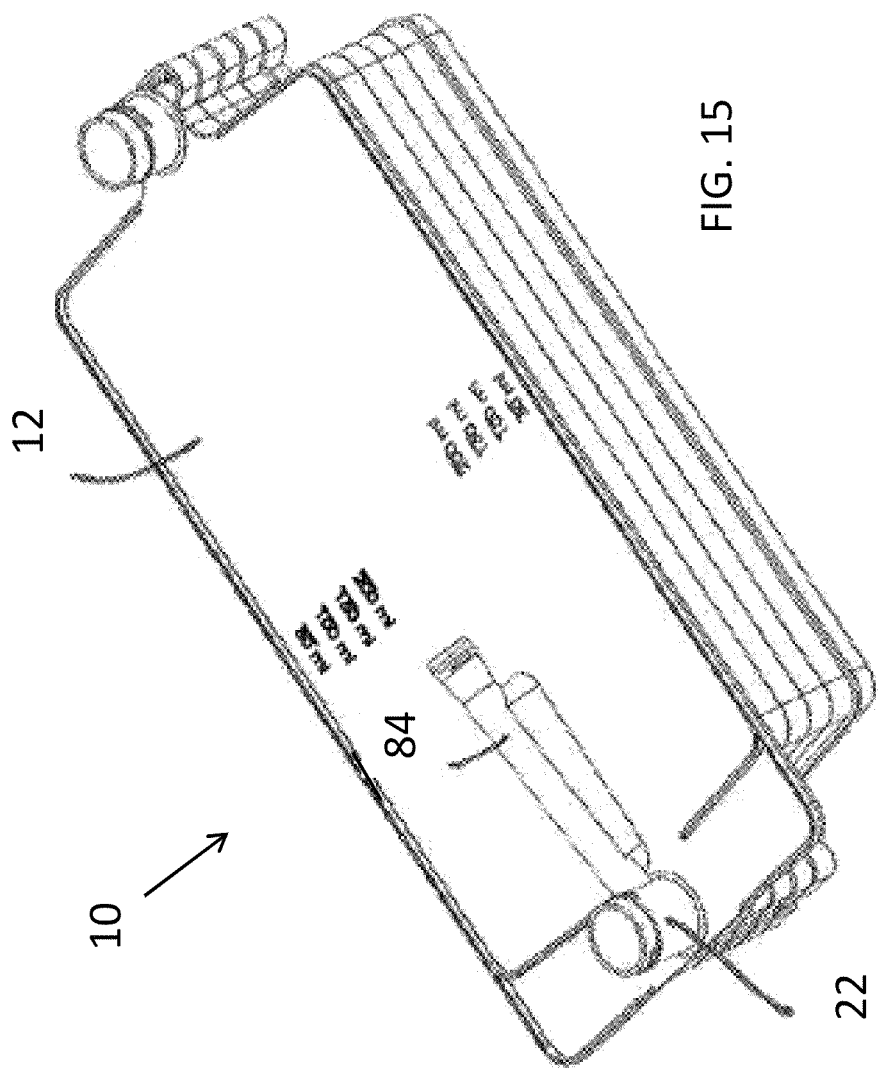

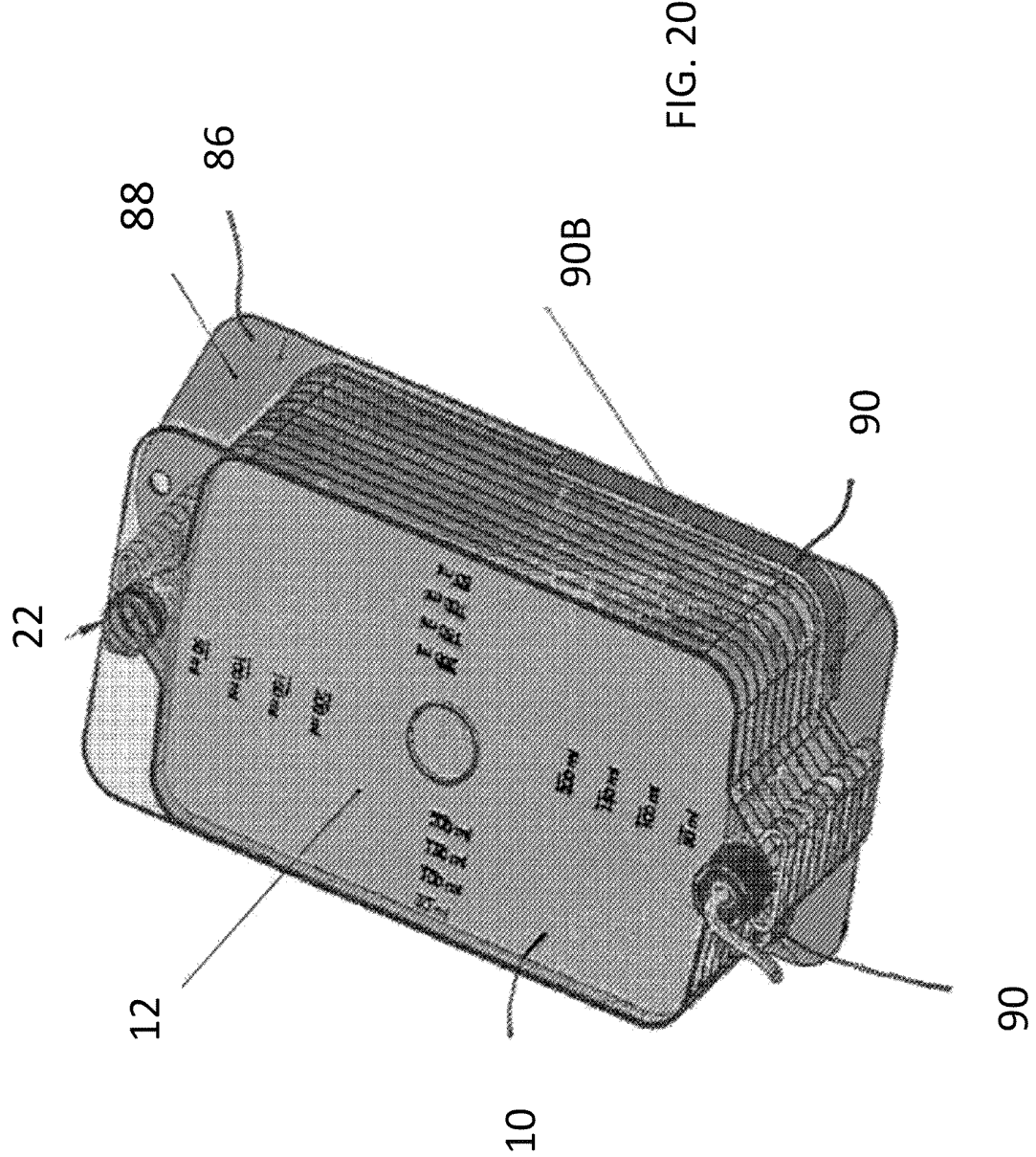

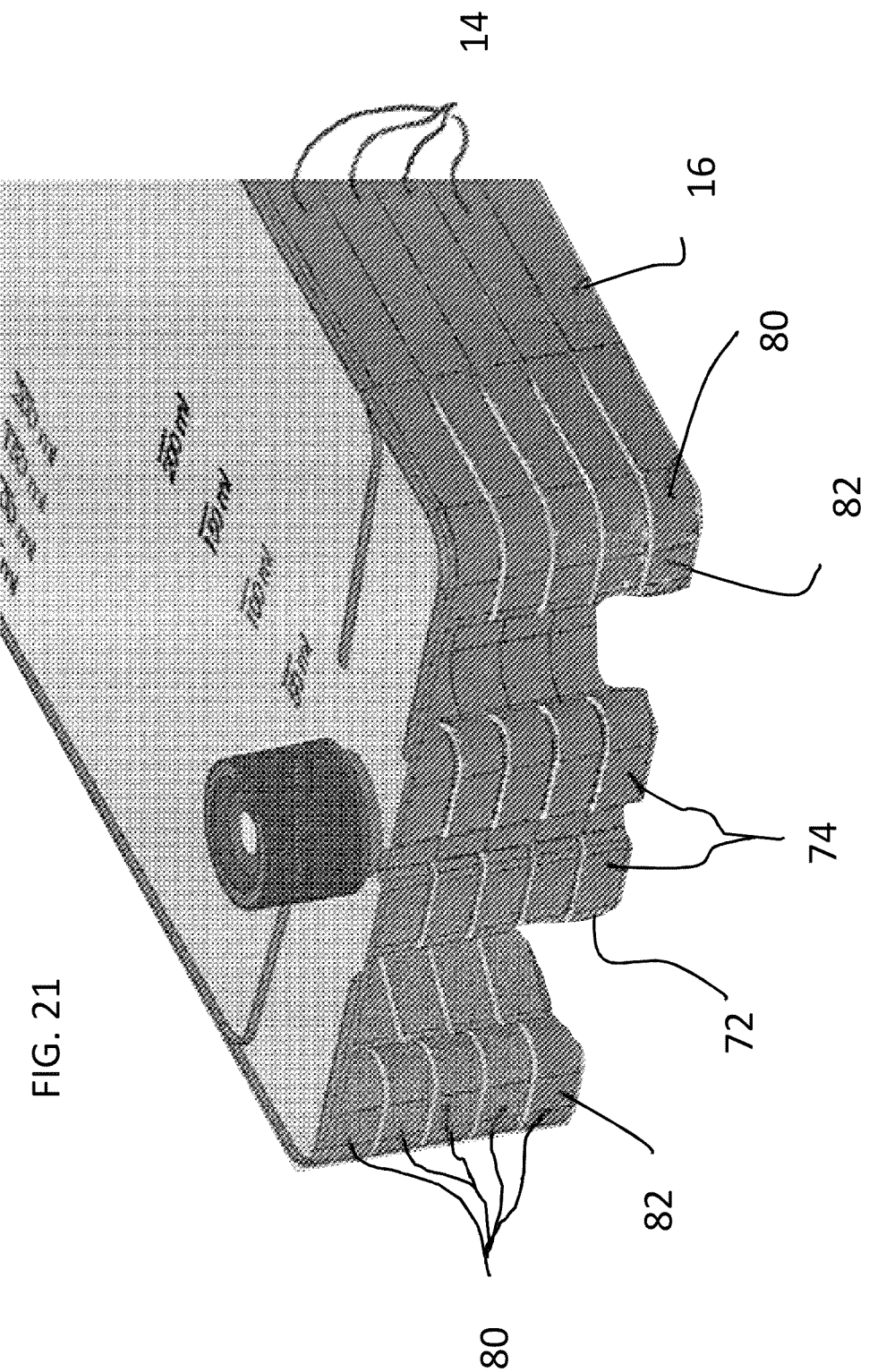

MULTI-LAYERED CELL CULTURE VESSEL WITH MANIFOLD GRIPS

This application claims the benefit of priority under 35 U.S.C. §119 of U.S. Provisional Application Ser. No. 61/719,593 filed on Oct. 29, 2012 the content of which is relied upon and incorporated herein by reference in its entirety.

FIELD OF THE INVENTION

This invention relates to multi-layered cell culture vessels and, more particularly, to manifolded multi-layered cell culture vessels.

BACKGROUND OF THE INVENTION

Prior art multilayer cell culture vessel designs (e.g. Corning CellSTACK™ and Nunc CELL FACTORY™) include a rectangular footprint (approximately 8"×13") with two ports located on corners of the vessel top near one end of the vessel. For this discussion, the word "end" describes the short, (e.g., 8"), dimension of the vessel and the word "side" describes the long, (e.g., 13"), dimension of the vessel. Prior art designs are typically provided in 1 layer (approx. 1.4" tall), 2 layer (approx. 2" tall), 5 layer (approx. 4" tall), 10 layer (approx. 7.5" tall), or 40 layer (approx. 28" tall) configurations. When using the prior art designs, the user must tilt the vessel so that a port corner is established as the lowest point so that all liquid will drain to that ported corner. This, combined with the generally rectangular shape of these vessels, creates a condition where the user must manage pouring from an unbalanced vessel. In addition, when these vessels, especially vessels having large numbers of cell culture chambers, are filled with cell culture media, they can very heavy and awkward to manipulate by hand. Therefore the present disclosure is provided.

SUMMARY OF THE INVENTION

The subject disclosure provides multi-layered cell culture vessels with grips molded into the vessel body and with fill and vent ports located in an alignment structured and arranged to improve gas exchange and fluid handling tasks. While a hand grip is contemplated, "grip" or "hand grip" are synonymous terms in this disclosure, and may refer to grips that are useful as a grip for a person manipulating the multi-layered cell culture device, or a robot gripping and handling the multi-layered cell culture device. In an embodiment, the fill and vent ports are integrated into the molded-in grips so that manual pouring of fluid (cells mixed in media and reagents) from the vessel mimics pouring of liquid from a pitcher. That is, in embodiments, the hand grips comprise the ports. In embodiments, the fill and vent ports are structured and arranged to open into into, and allow fluid to flow through each hand grip area which acts as an open path for the delivery and removal of fluid from each layer of the vessel, and from the vessel itself. In an embodiment, this open path for delivery and removal of fluid is created by a manifold which provides a liquid containment chamber to both distribute fluid evenly amongst all of the vessel compartments (i.e. layers) and to act as fluid mixing chambers. In an embodiment, the vessel comprises a base, at least one insert layer, and a lid that are assembled to form a leak proof, closed vessel for the culturing of cells. In embodiments, the lid includes vent and fill ports for the introduction of liquid media, reagents, and suspended cells into the vessel. The vessel may be closed with vented or closed screw caps to form a leak tight cell culture environment. Additional accessory items may also be present, in embodiments. Such accessories include caps, caps having vents, caps having integrated tubing nipples, caps with attached tubing, tubing, liquid and air filter sets, media bags, etc. may be used with the vessel to create an open or closed loop cell culture system.

The present disclosure provides a cell culture vessel having hand grips. The hand grips dramatically improve the functionality of the vessel within the cell culturing workflow and laboratory environment. Current cell culture vessels are awkward to handle, transport within the laboratory environment, and pour liquid from because they lack any handle or grips to facilitate these critical process functions. The vessel disclosed herein remedies this through the inclusion of grips molded into the vessel. As a result, the user can better handle the liquid filled vessel. Because the design includes one grip located on each end of the vessel the user can more readily balance the liquid filled vessel during pouring operations. In embodiments, the grips are aligned along a center line of the vessel. In embodiments the grips are aligned along a side of the vessel. The location of the grips ensures that the shifting center of mass of the liquid filled vessel always falls between the two grips thereby improving the user's ability to balance and handle the vessel and to control the pouring of liquid from the vessel. The location of the grips on opposite ends of the vessel simplifies the user's effort when manually placing and removing the vessel from a location, such as a laminar flow hood, incubation chamber or other laboratory storage location. Additionally, the grip and grip placement on the vessel improves the user's ability to move the vessel without sloshing the liquid within the vessel because the user has a more natural grip on the vessel and because the grips provide the user with the ability to more easily balance the vessel side-to-side and front-to-back. This is possible because the plane of the center of mass of the vessel is located between the two grips and because the grips provide a natural hand position to enable coordinated manual tipping and twisting of the vessel to maintain the level of the bottom plane of the vessel during manual transport.

In addition, as will be described, the disclosure incorporates spillways for each layer at the manifold chamber so as to distribute liquid evenly amongst the layers. In embodiments, the manifold acts as a liquid and gas exchange manifold through the inclusion of spillways for each layer at the grip-to-layer interface point. It is envisioned that users may use this feature to mix cell and cell growth media. By tilting the liquid filled vessel toward each end several times, even mixing of cells and media is readily accomplished. Further, the location of the grips at each end of the vessel provides a natural grip for the transport of the vessel while the media is evenly distributed amongst the layers. The liquid is evenly distributed to each layer by simply tilting the vessel on one end and then laying the vessel down on its side. The grip locations are then situated for the user to manually lift and transport the vessel while maintaining this even distribution of liquid among the vessel layers. Once in the desired location, such as in an incubator, the user simply places the vessel down on its side and then tilts the vessel onto its bottom to lay the liquid down upon each layer.

In embodiments, the disclosed vessel maintains the functionality of currently available cell culture vessels such as: multiple layers of cell culture surfaces within one leak proof vessel, a simple method to evenly distribute the fluid within the vessel to each layer to distribute a similar distribution of cell across each growth surface, and fill and drain ports for the introduction and removal of media and cells from the vessel. In addition, the disclosed vessel provides many additional benefits which are described herein.

BRIEF DESCRIPTION OF THE DRAWINGS

FIG. 15 is a perspective view of an embodiment of the lid of the disclosed multi-layered flask, showing an optional access port associated with a port.

FIG. 20 is another perspective view of an embodiment of the multi-layered flask, engaged into an embodiment of a bracket.

FIG. 21 is a perspective view of another embodiment of the grips, in an embodiment of the multi-layered flask, showing additional support members.

DETAILED DESCRIPTION OF THE INVENTION

The lack of a handle or grips on prior art multi-layered cell culture vessels forces a user to hold the vessel either with their hands grasping the lid and base with their thumb and fingers respectively or with their open hand and/or arm placed underneath the bottom of the vessel during transport or pouring operations. These methods affect the ability of the user to have good control of the vessel during transport and pouring. Pouring liquid from the prior art vessels is made difficult because the vessels include no handle or grip and the center of mass of the filled vessel is offset from the pouring port. In addition, because the ports on the prior art multilayer cell culture vessels are located along a single end of the vessel top, open loop pouring or transfer of vessel contents into another vessel (flask, bottle, etc.) is difficult. In embodiments described herein, a cell culture vessel is provided which has hand grips. In embodiments, the vessel has multiple ports located on opposite ends of the vessel. In embodiments, the hand grips comprise the ports. In embodiments, the ports are aligned along a midline of the cell culture vessel. In additional embodiments, the ports may be aligned along a side of the vessel.

In additional embodiments, the vessel may also have protruding supports on one or more end of the vessel to allow the vessel to stand on its end in a secure manner. In addition, the vessel may be provided with a bracket that allows the vessel to be mounted on a surface. In embodiments the bracket may allow the multi-layered vessel to be mounted to a vertical surface.

Figure 1:
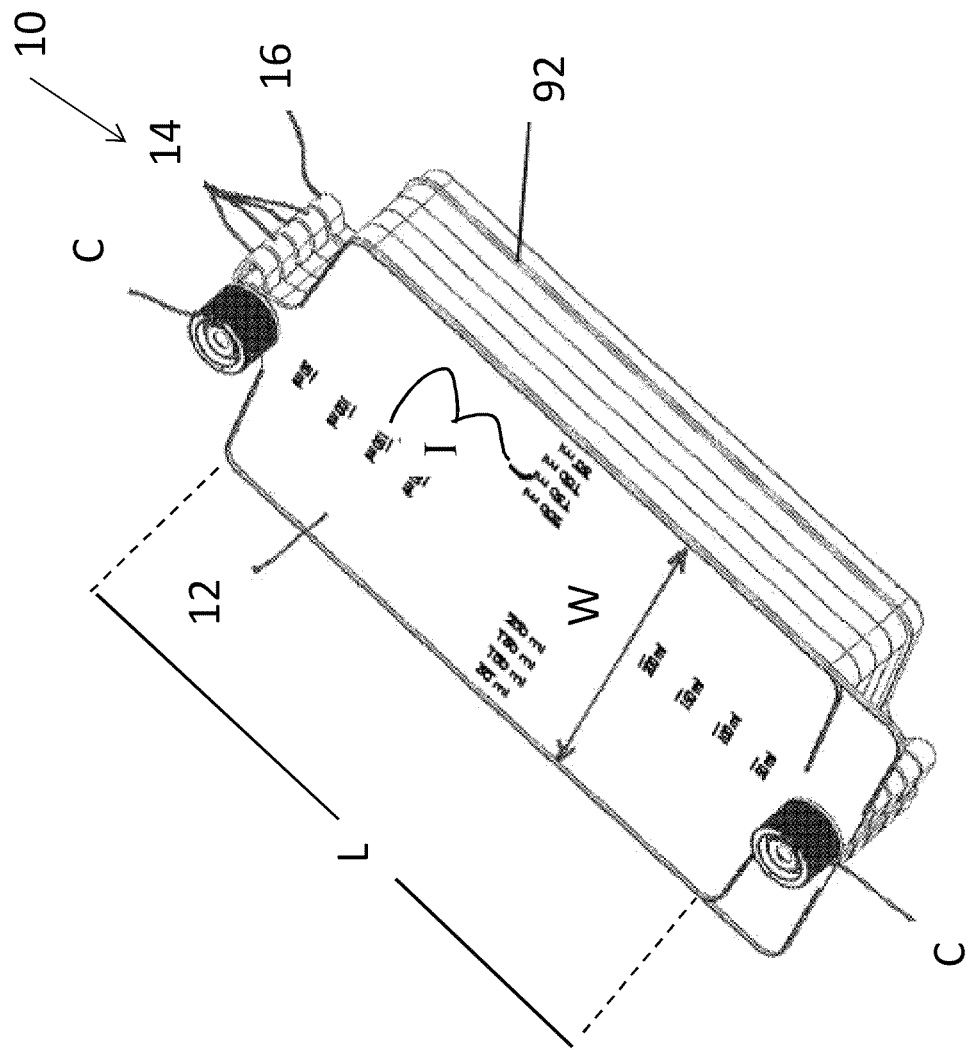
FIG. 1 is a perspective view of a multi-layered cell culture vessel with grips and ports closed by caps according to embodiments.

Turning now to the figures, embodiments of a multi-layered cell culture vessel is shown and generally designated with the reference numeral 10. As shown in FIGS. 1-4, the vessel 10 generally includes a lid 12, at least two insert layers 14 and a bottom 16. As shown in the figures, in embodiments, the vessel is generally elongated. That is, the length (L, as shown in FIG. 1) is generally greater than the width (W, as shown in FIG. 1) of the vessel.

Figure 5:
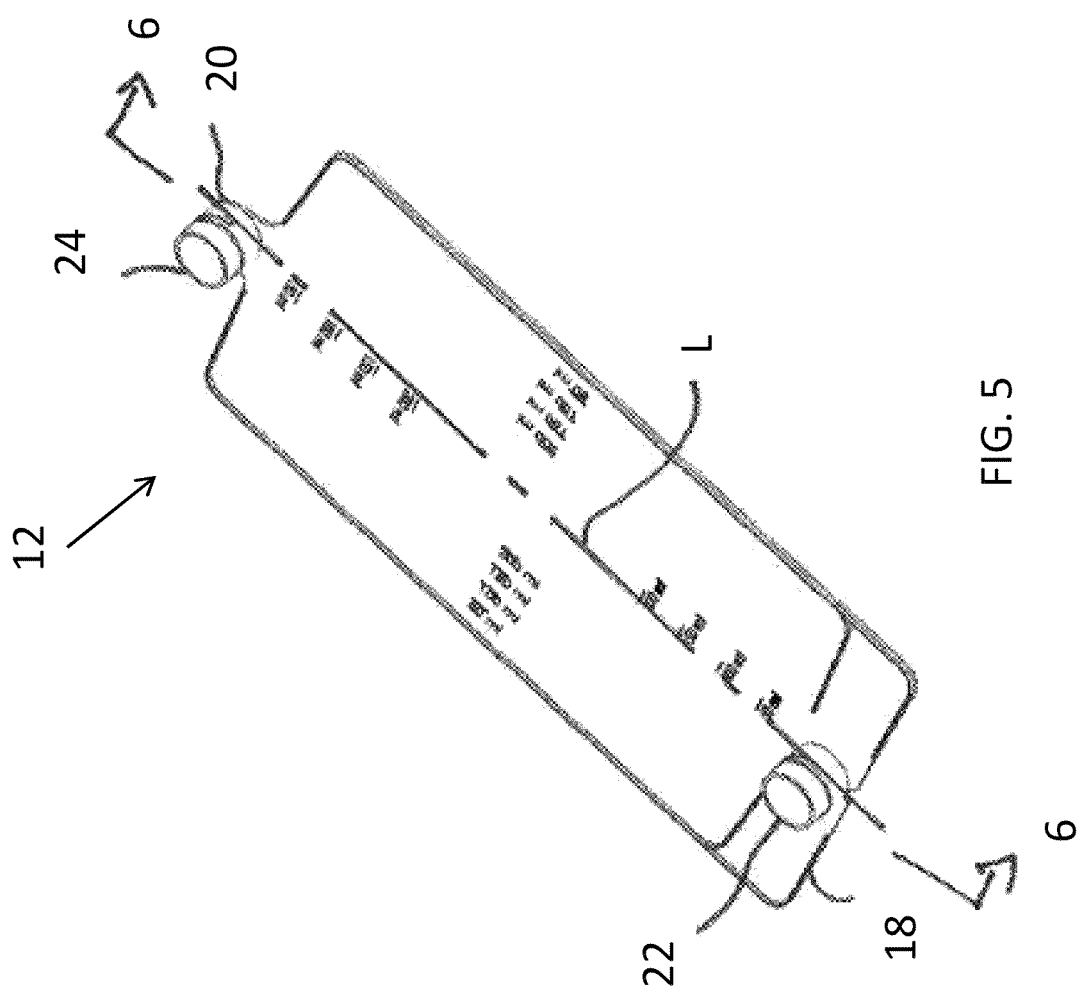
FIG. 5 is a perspective view of a lid useable with the multi-layered cell culture vessel according to embodiments.
Figure 6:
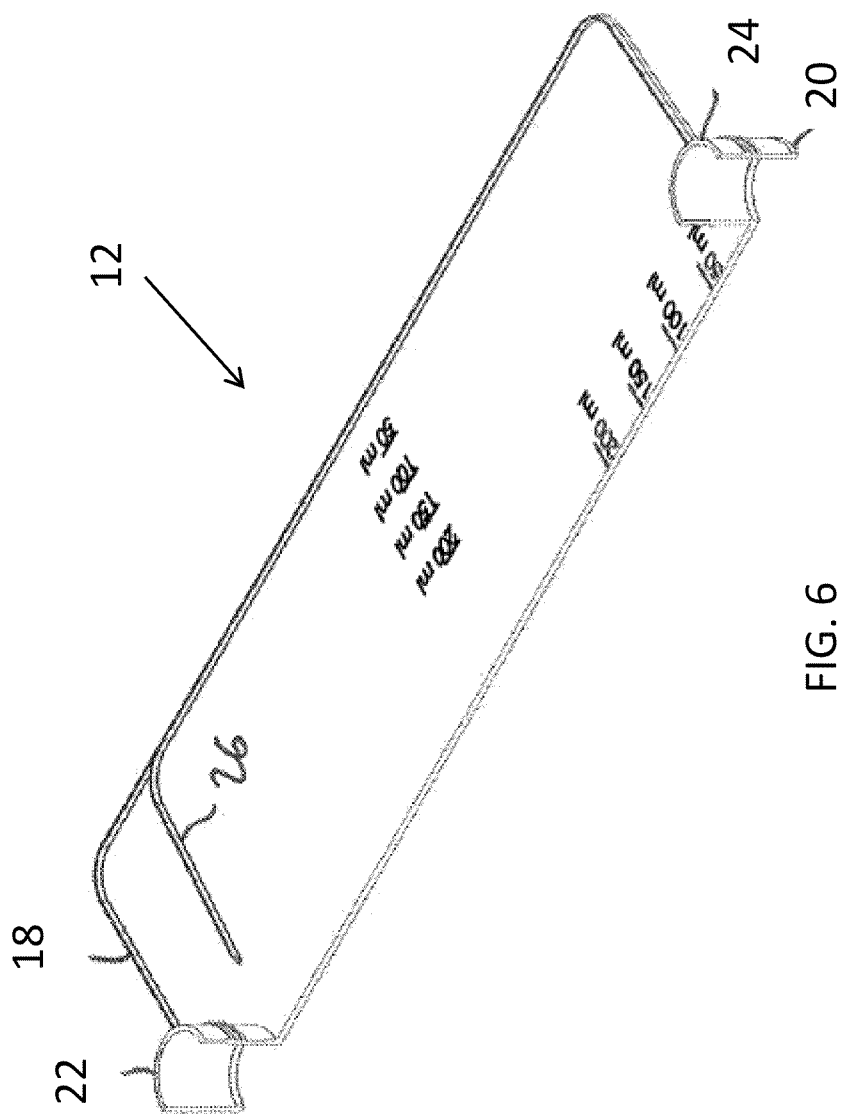
FIG. 6 is a cross-sectional view of a lid useable with the multi-layered cell culture vessel according to embodiments taken along line 6-6 of FIG. 5.

Embodiments of the lid are illustrated in FIGS. 5 and 6. As shown in FIGS. 5 and 6, the lid 12 is elongated to extend along a longitudinal axis L between first and second ends 18, 20. The longitudinal axis L bisects the lid 12. In embodiments, first and second ports 22, 24 extend through the lid 12 and are located spaced apart along the longitudinal axis L. In additional embodiments, the first and second ports 22, 24, my be located along a common axis offset from the vessel's center line. In embodiments, the first and second ports 22, 24, may be threaded or otherwise configured to accept a cap or other closure member C thereon.

In embodiments, the first end 18 is an apron which extends transversely outwardly from the longitudinal axis L. In embodiments, the first end 18 is as wide as a transverse width W (FIG. 1) of the vessel 10. In addition, in embodiments, the second end 20 be of a lesser length than the transverse width W.

In some embodiments, the lid 12 may be generally plate shaped with the first and second ports 22, 24 extending upwardly therefrom. In addition, cooperating features may be provided on the lid 12 and the bottom 16 formed to provide alignment and integrity in stacking. For example, the lid 12 may be provided with ribs 26 which are configured to be received in corresponding channels formed on the bottom 16 of an adjacent upper stacked vessel 10.

Figure 7:
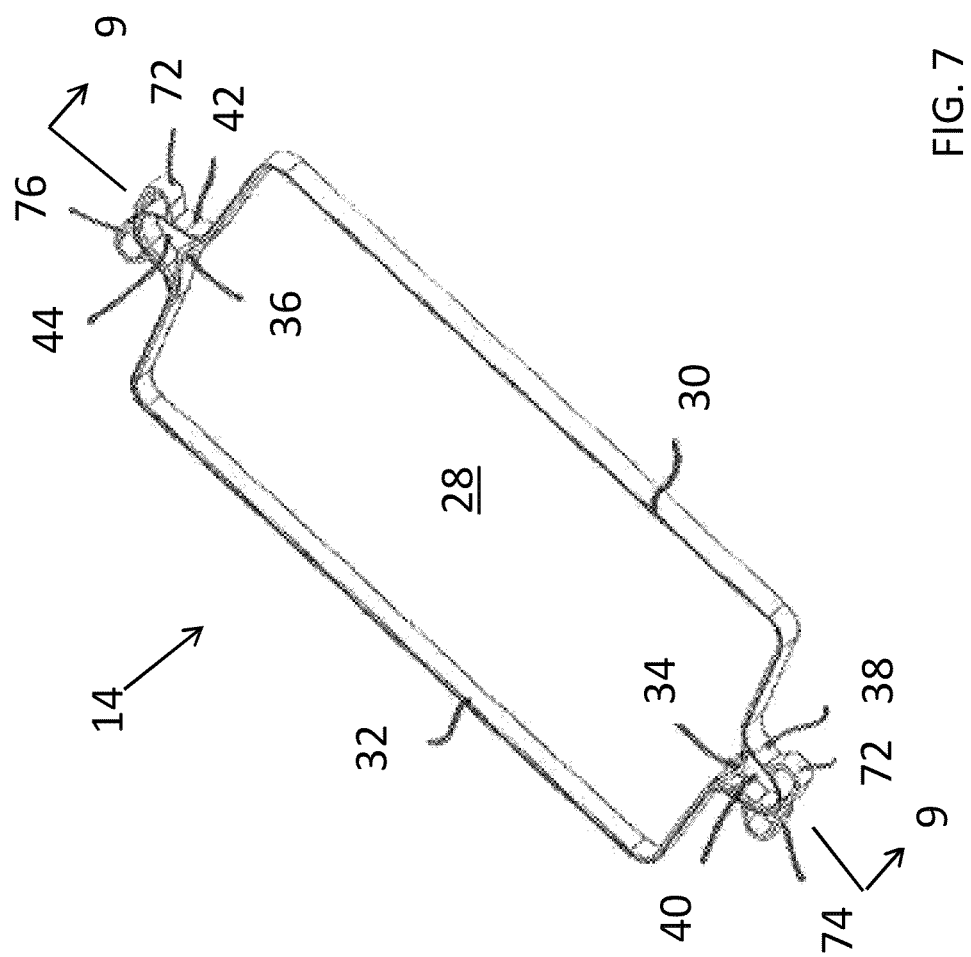
FIG. 7 is a perspective view of an insert layer in embodiments of the disclosure.
Figure 8:
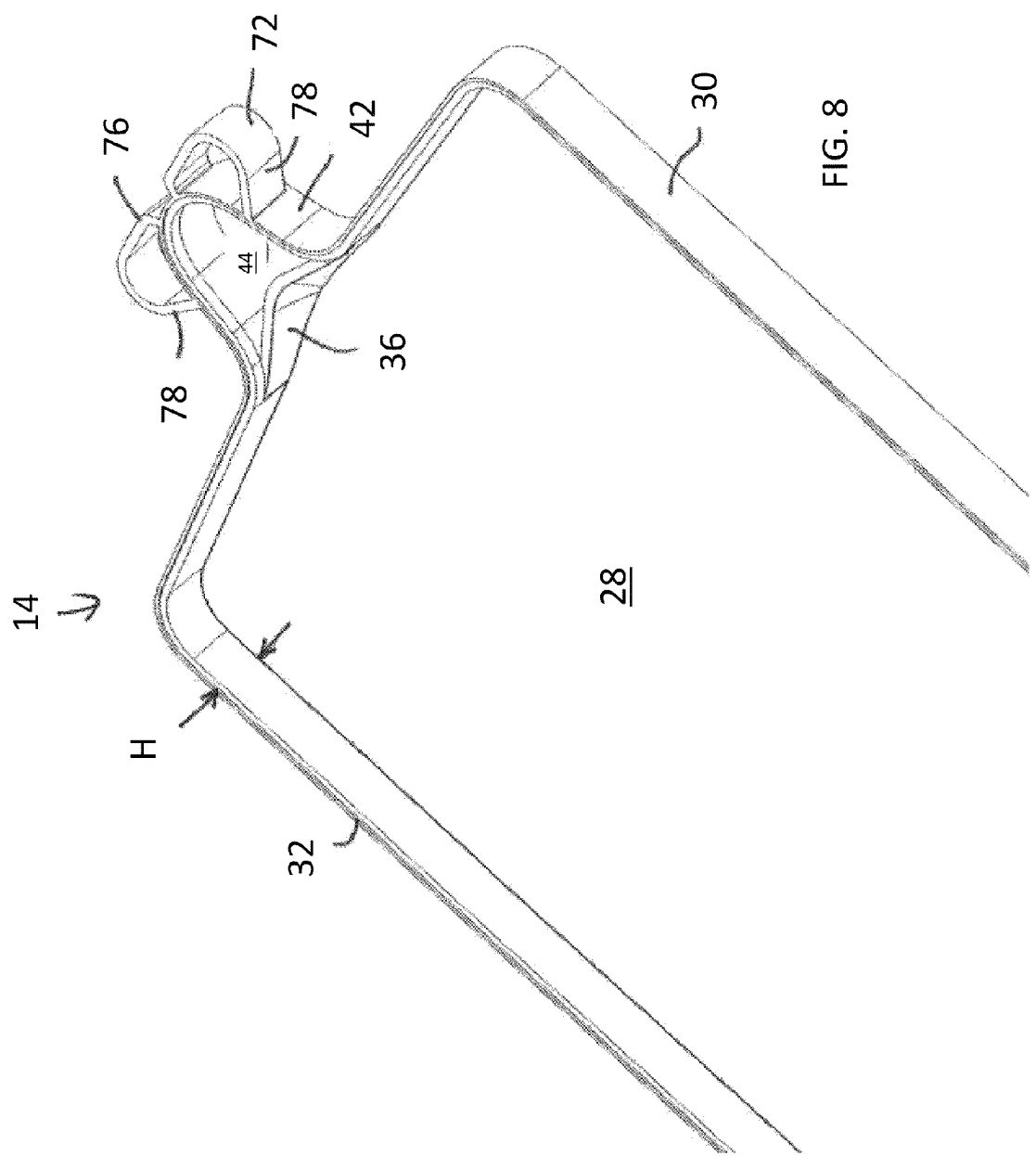
FIG. 8 is an enlarged view of a portion of the insert layer shown in FIG. 7.
Figure 9:
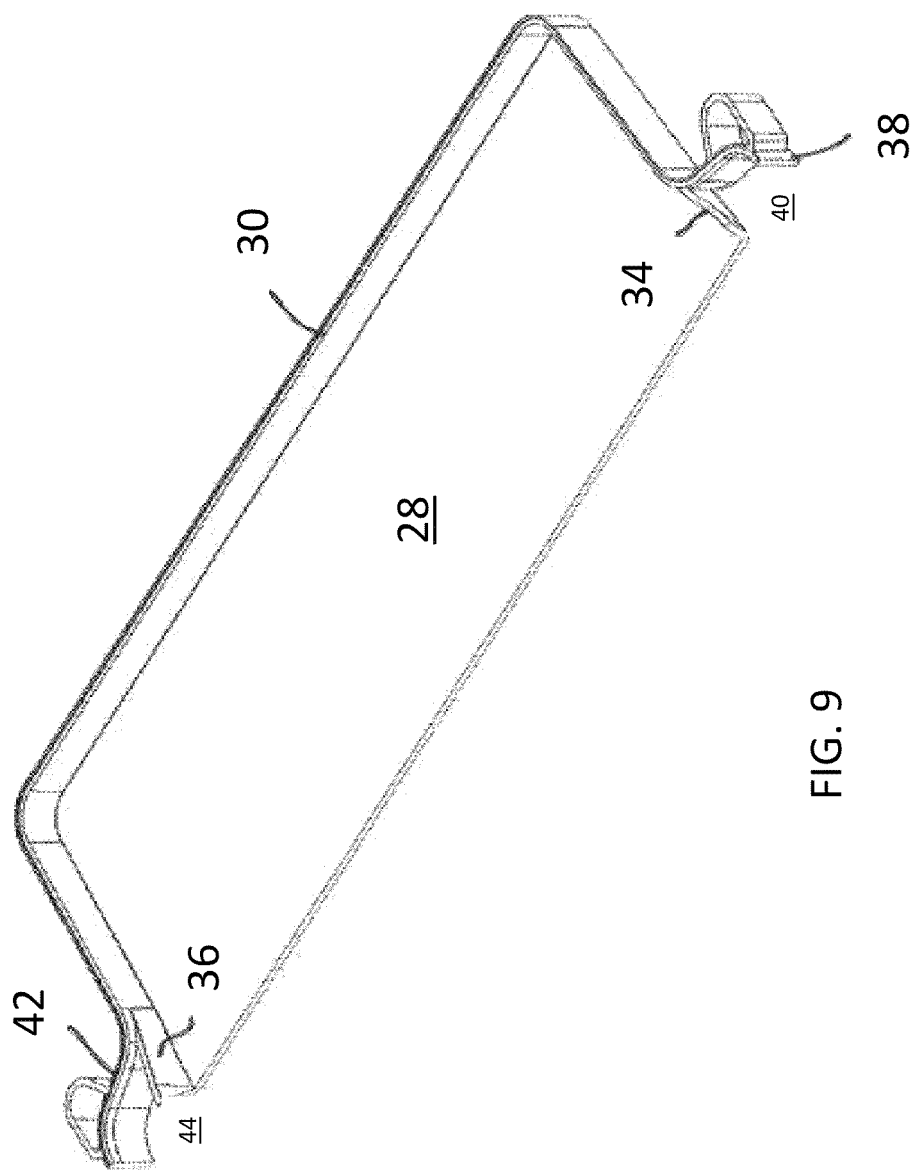
FIG. 9 is a cross-sectional view of an insert layer taken along line 9-9 of FIG. 9.

As shown in FIGS. 7-9, each of the insert layers 14 includes a generally planar base 28. First and second upstanding rim portions 30, 32 extend from the base 28. In addition, first and second upstanding spillways 34, 36 also extend from the base 28. The first and second rim portions 30, 32 extend from the base 28 to a height H. The first and second spillways 34, 36 extend from the base 28 a height less than the height H. Also, the first spillway 34 extends between the first and second rim portions 30, 32, and the second spillway 34, also extends between the first and second rim portions 30, 32. Preferably, the first and second rim portions 30, 32 and the first and second spillways 34, 36 collectively define a wall for containing cell media on the base 28 during use.

Each of the insert layers 14 also includes a first collar 38 which extends outwardly from the base 28 adjacent to the first spillway 34. The first collar 38 defines a first passageway 40 therethrough. Also, a second collar 42 extends outwardly from the base 28 adjacent to the second spillway 36. The second collar 42 defines a second passageway 44 therethrough. As will be discussed in more detail below, the first passageway 40 is located relative to the first spillway 34 so that cell media may be transferred over the first spillway 34 in and out of the first passageway 40 as needed. The second spillway 36 and the second passageway 44 are similarly configured.

Figure 10:
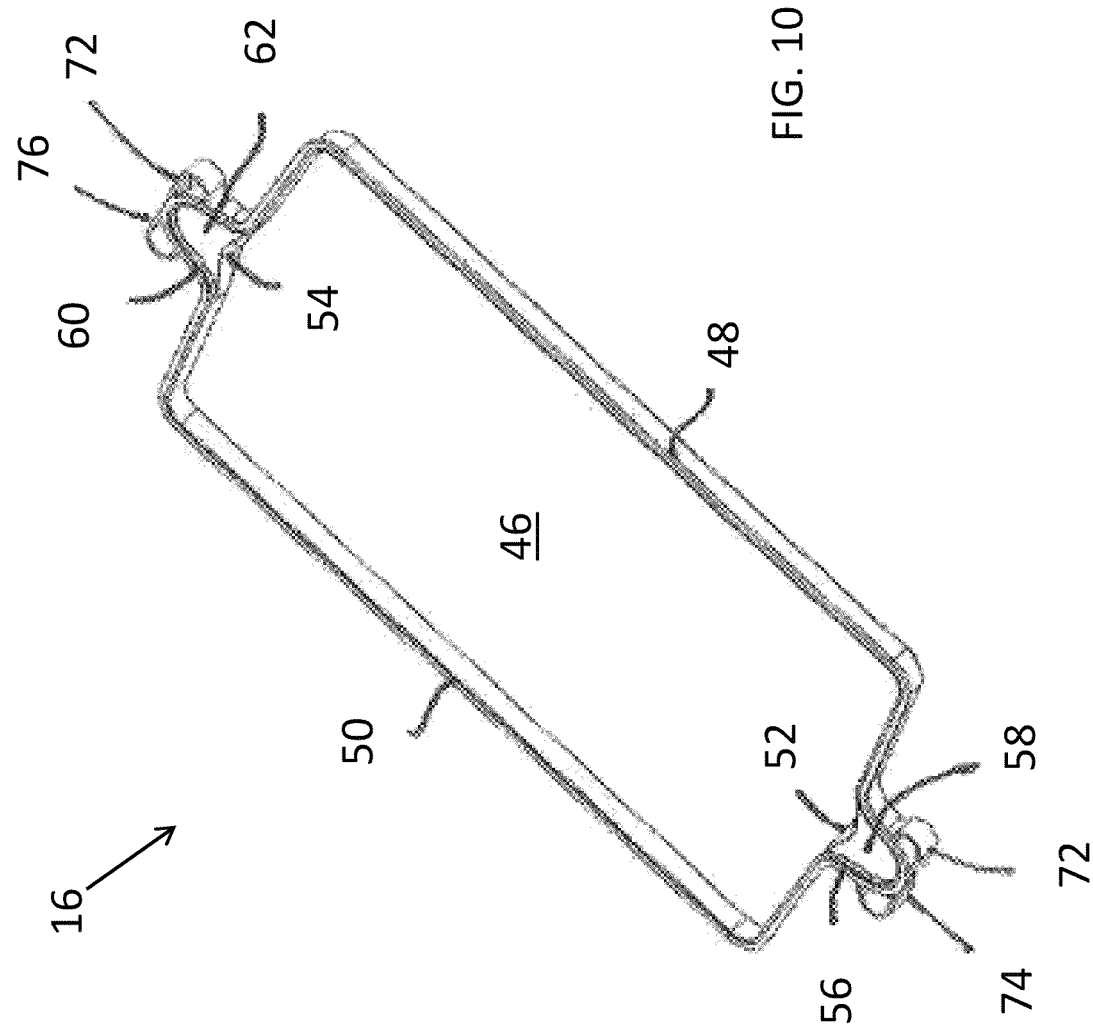
FIG. 10 is a perspective view of a base according to embodiments of the disclosure.
Figure 11:
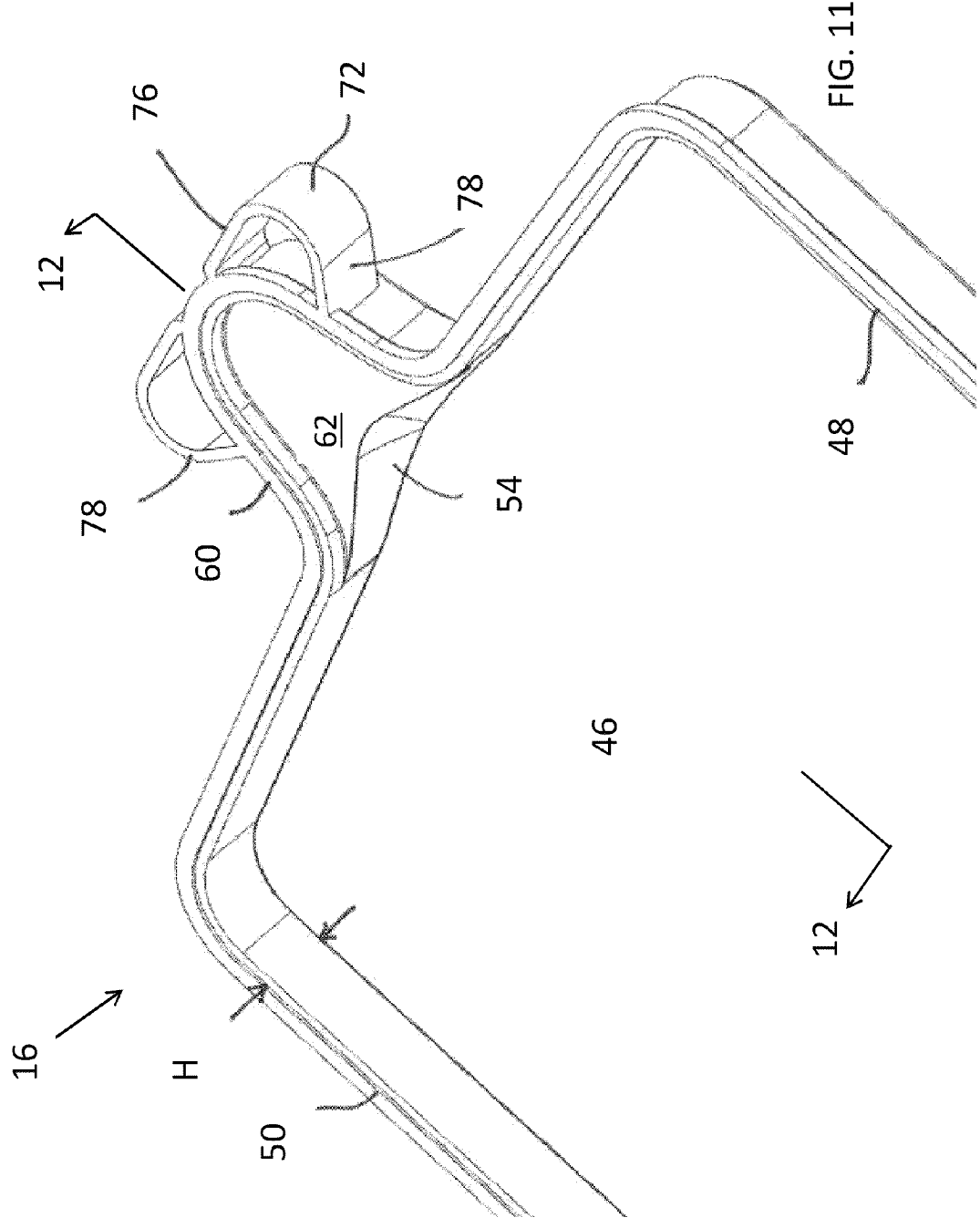
FIG. 11 is an enlarged view of a portion of the base shown in FIG. 10.
Figure 12:
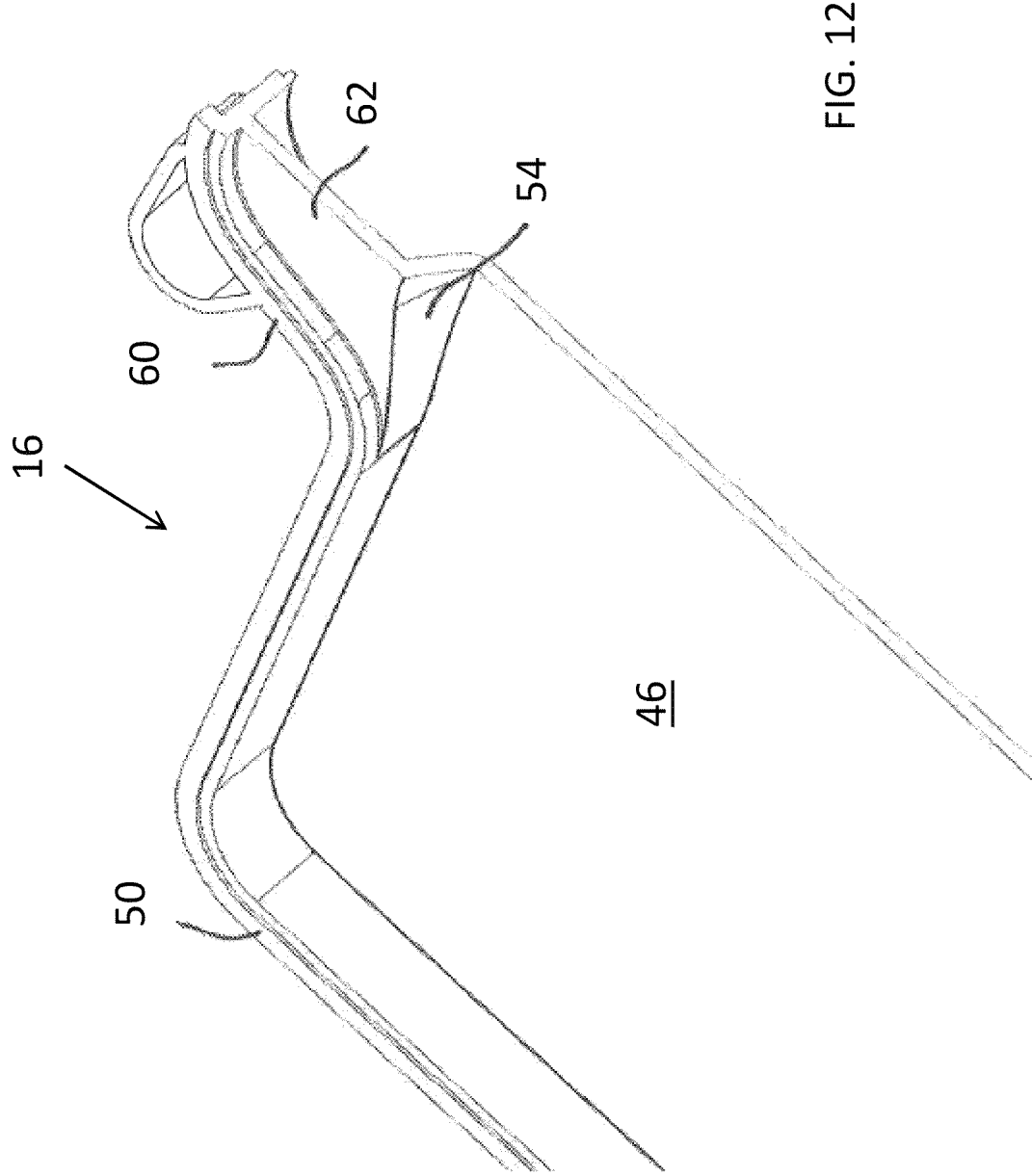
FIG. 12 is a cross-sectional view of the enlarged portion of the base shown in FIG. 11, taken along line 12-12 of FIG. 11.
Figure 13:
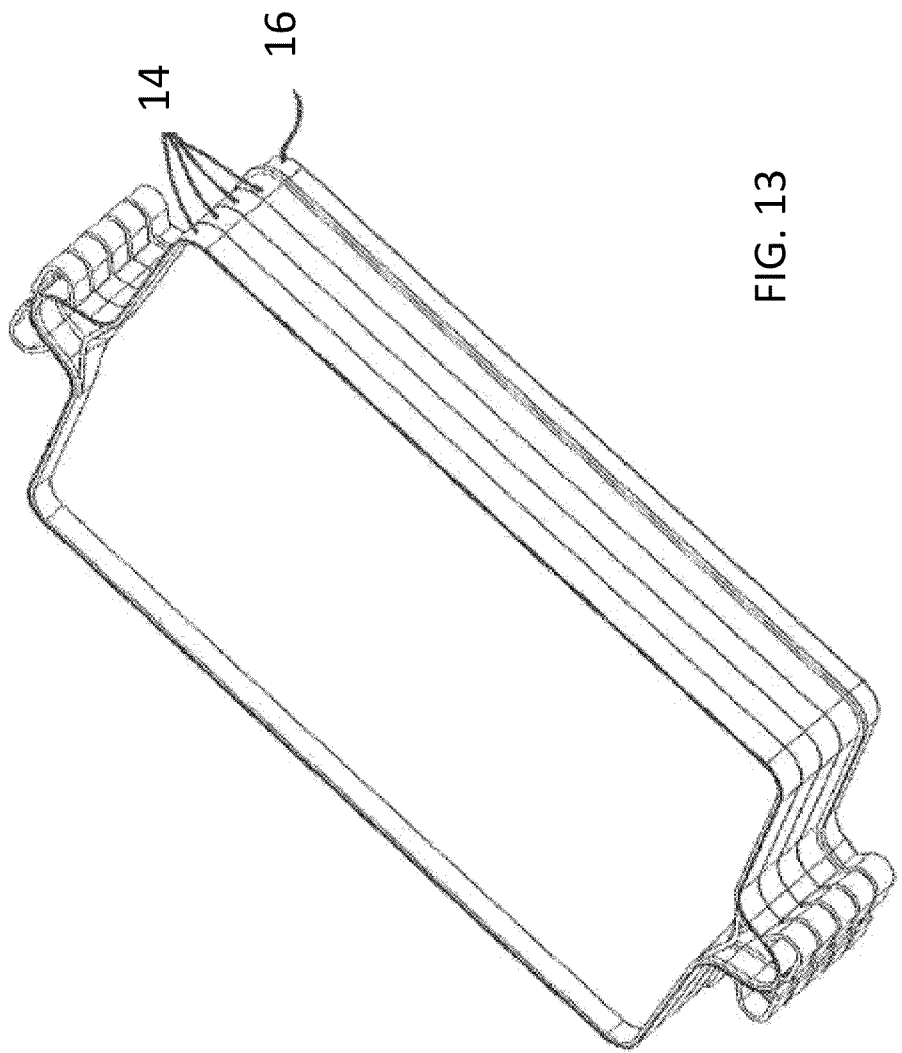
FIG. 13 shows a plurality of insert layers and a base in stacked, assembled arrangement, according to embodiments.

As shown in FIGS. 10-12, the bottom 16 includes a generally planar base 46. First and second upstanding rim portions 48, 50 extend from the base 46. In addition, first and second upstanding spillways 52, 54 also extend from the base 46. The first and second rim portions 48, 50 extend from the base 46 the height H. The first and second spillways 52, 54 extend from the base 46 a height less than the height H. Also, the first spillway 52 extends between the first and second rim portions 48, 50, and the second spillway 54 also extends between the first and second rim portions 48, 50. Preferably, the first and second rim portions 48, 50 and the first and second spillways 52, 54 collectively define a wall for containing cell media on the base 46 during use.

The bottom 16 also includes a first dish 56 which extends outwardly from the base 46 adjacent to the first spillway 52. The first dish 56 defines a solid first containment surface 58. Also, a second dish 60 extends outwardly from the base 46 adjacent to the second spillway 54. The second dish 60 defines a second containment surface 62.

Figure 3:
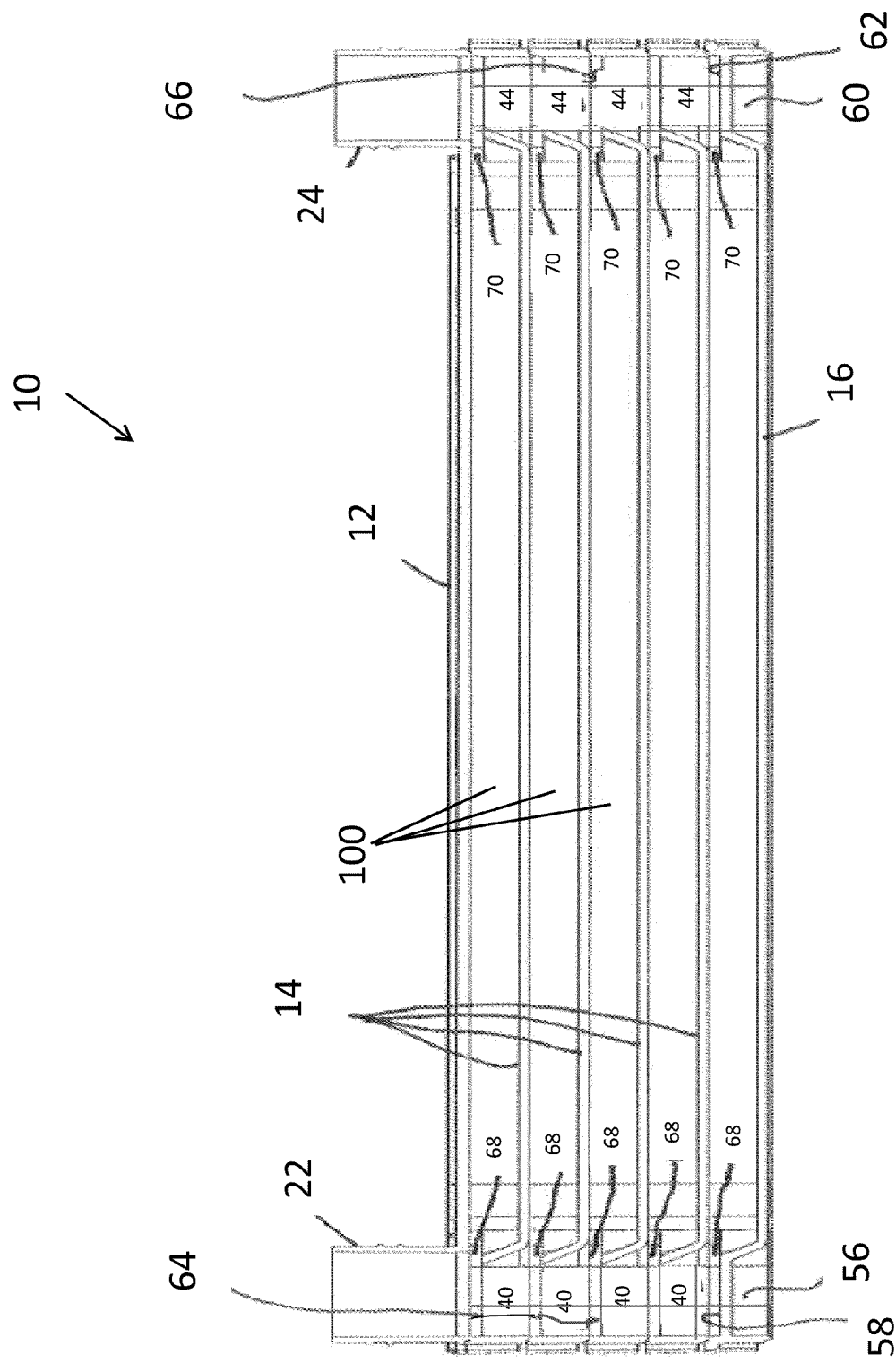
FIG. 3 is a cross-sectional view of a multi-layered cell culture vessel taken along line 3-3 of FIG. 2.
Figure 4:
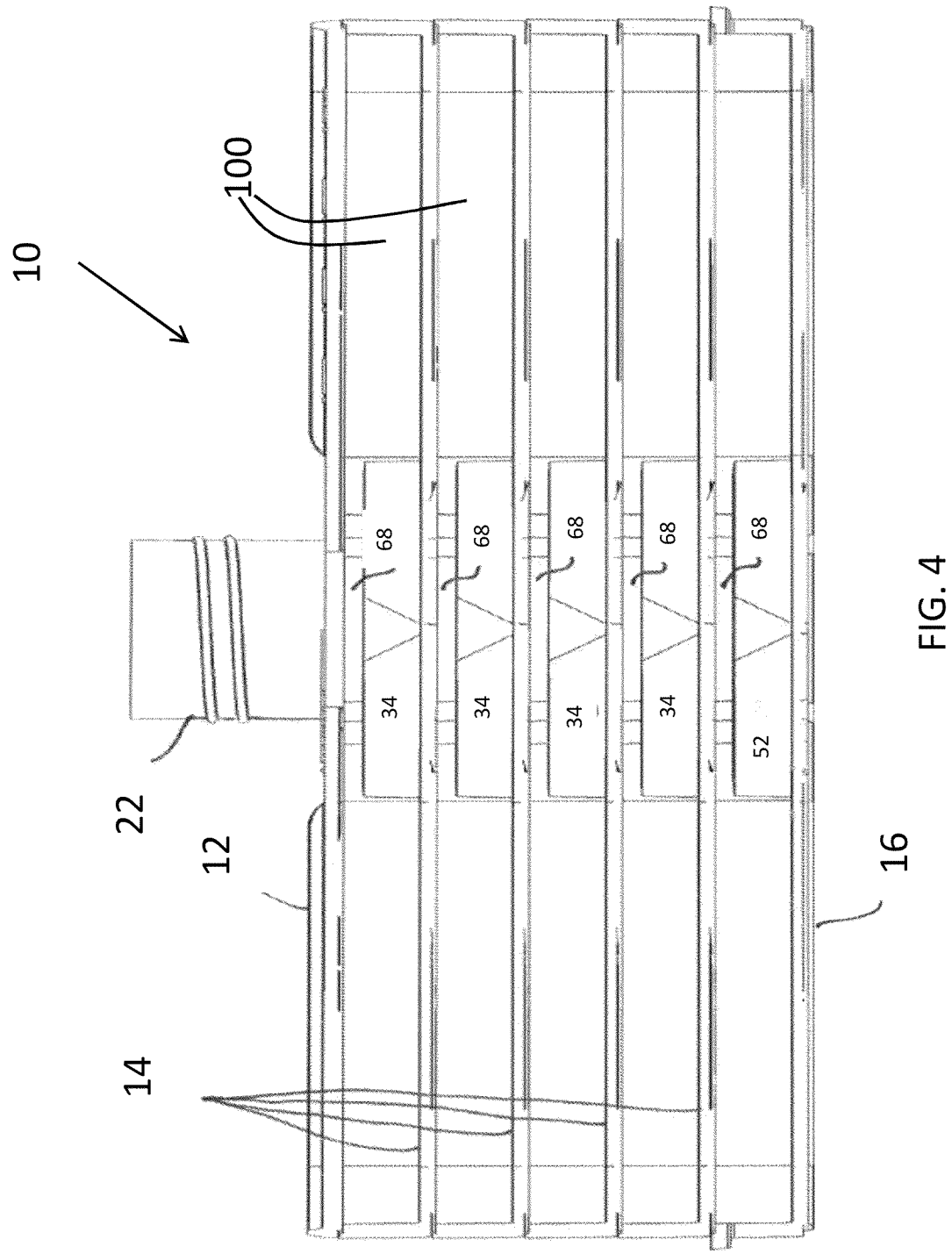
FIG. 4 is a cross-sectional view of a multi-layered cell culture vessel taken along line 4-4 of FIG. 2.

To form the vessel 10, the lid 12, each of the insert layers 14, and the bottom 16 are provided in a stacked arrangement with each of the insert layers 14 being located between the lid 12 and the bottom 16. In embodiments, a plurality of the insert layers 14 is utilized. The lid 12, the insert layers 14, and the base 16 enclose a volume within the vessel 10. Portions of the lid 12, the insert layers 14 and the base 16 collectively define the exterior of the vessel 10. In the stacked arrangement, as best shown in FIG. 3, the first port 22 is in axial alignment with the first passageway 40 of each of the insert layers 14 and with the first dish 56 of the bottom 16 (including the first containment surface 58), and the second port 24 is in axial alignment with the second passageway 44 of each of the insert layers 14 and with the second dish 60 of the bottom 16 (including the second containment surface 62). With this arrangement, a first collective passageway 64 is defined through the insert layers 14 in communication with the first port 22. This passageway is a manifold. The bottom of the first collective passageway 64 being sealed by the first dish 56, in particular, by the first containment surface 58. In similar configuration, a second collective passageway 66 is formed through each of the insert layers 14 in communication with the second port 24 which is sealed at its bottom by the second dish 60, in particular, by the second containment surface 62. The first and second collective passageways 64, 66 provide manifold communication with the individual volumes enclosed by each of the insert layers 14 and the base 16, while being spaced therefrom.

Liquid which enters a port (see, for example 22 in FIG. 3) flows into the collective passageway or manifold 64, and then into each cell culture chamber 100.

In the stacked arrangement, the insert layers 14 are secured to one another in a fluid-tight manner. In embodiments, the insert layers 14 are stacked so that the base 28 of an upper stacked insert layer 14 rests on the first and second rim portions 30, 32 of a lower stacked insert layer 14. A liquid-tight seal, as is known in the art, is caused to be defined therebetween at the points of engagement, such as through adhesion, fusion and/or mechanical interlocking. Gaskets or other sealing members may be interposed as needed. With this arrangement, first and second gaps 68, 70 are defined between the first and second spillways 34, 36 of a lower stacked insert layer 14 and the base 28 of an upper stacked insert layer 14. The first collective passageway 64 is in communication with the first gaps 68 of each of the insert layers 14, while the second collective passageway 66 is in communication with the second gaps 70 of each of the insert layers 14.

Liquid which enters a port (see, for example 22 in FIG. 3) flows into the collective passageway or manifold 64, and then into each cell culture chambers 100. In an embodiment, liquid which enters a port 22, flows into a collective passageway or manifold 64 and then flows into each cell culture chamber over a spillway 34 (see FIG. 7). In embodiments the spillway is angled.

In the stacked arrangement, the bottom 16 is secured to the lowest stacked insert layer 14 in the same manner as described above with respect to the stacked insert layers 14. In particular, the first and second rim portions 48, 50 of the bottom 16 are secured in fluid-tight manner to the base 28 of the lowest stacked insert layer 14. In addition, the first and second gaps 68, 70 are formed above the first and second spillways 52, 54, respectively, of the bottom 16 in similar manner to that described above, the first and second collective passageways 64, 66, respectively, being in communication with these gaps as well. In an assembled state, the lid 12 is secured to the first and second rim portions 30, 32 of the uppermost stacked insert layer 14.

In embodiments, each of the first collars 38 and the first dish 56 have the same footprint so as to be superimposed in a stacked arrangement. In embodiments, adjacent collars 38 and first dish 56 can be secured to one another in a fluid-tight manner, in the same manner used in securing the insert layers 14 and the base 16 discussed above. In embodiments, the second collars 42 and the second dish 60 can be configured and secured in similar manner.

In embodiments, first and second rim portions 30, 32 of each of the insert layers 14 and that the first and second rim portions 48, 50 of the bottom 16 are all provided at the height H. It is also preferred that the base 28 of each of the insert layers 14 and that the base 46 of the bottom 16 be dimensioned in the same manner so as to define the same footprint. With the same dimensioning between the insert layers 14 and the bottom 16, the same volume may be defined for each layer for cell culturing. This is desired to allow for partitioning of cell culture media evenly amongst the insert layers 14 and the bottom 16.

The lid 12, the insert layers 14 and the base 16 may be formed with any material compatible with the intended cell culturing. Preferably, the lid 12, the insert layers 14 and the base 16 are formed of a thermoplastic material, e.g., by molding. In addition, various portions of the lid 12, the insert layers 14, and the base 16 may be treated, or otherwise prepared, to enhance cell adhesion or adherence-resistance, as desired.

In use, cell media may be introduced into the vessel 10 through one or both of the first and second ports 22, 24. In an embodiment, the second port 24 may be utilized, particularly with the second end 20 being of limited length. In embodiments, the constituent components of the vessel 10, namely the lid 12, the insert layers 14 and the bottom 16, all may be formed of transparent material. With the second end 20 being of limited length, there is minimal visual obstruction as cell media is introduced into the second collective passageway 66. With filling the vessel 10 through the second port 24, venting is provided for the vessel 10, particularly, through the first and second gaps 68, 70 of the insert layers 14, through the first collective passageway 64, and the first port 22. Venting may be provided in similar manner, but in a reverse direction, if cell media is introduced through the first port 22 (i.e., venting through the first and second gaps 68, 70 of the insert layers 14, through the second collective passageway 66, and the second port 24). Cell media may be introduced in any known manner, such as by pouring, pipetting, or introduction through a tube or other conduit, such as through gravity feed or pumping action. Indicia I may be provided on the lid 12 to evaluate the amount of cell media introduced into the vessel 10. Advantageously, the first and second collective passageways 64, 66 act not only to provide for distribution amongst the insert layers 14 and the bottom 16 of the cell media, but also act as mixing chambers for the cell media. Once filled, the vessel 10 may be caused to be agitated with a back and forth motion, caused to stand on its side and returned to an upright position with equilibration of the cell media amongst the insert layers 14 and the bottom 16.

The vessel 10 may be held in a vertical alignment during filling, e.g., via a tube-fitted closure C (such as that shown in FIG. 19) attached to the first port 22. In this arrangement, a vented closure C may be mounted to the second port 24 to contain liquid media in the vessel 10, yet allow venting, with filling through the first port 22. In embodiments, the vessel 10 is configured to be self-supporting to stand in this vertical alignment. The first end 18 of the lid 12, the first collars 38, and the first dish 56 may collectively define a resting surface for the vessel 10 to be supported in vertical alignment. To enhance the ability to maintain the vessel 10 in a vertical alignment, it is preferred that each of the first and second collars 38, 42 and the first and second dishes 56, 60 is provided with at least one outwardly extending lobe 72. Each of the lobes 72 on the first collars 38 defines a generally flat surface 74 spaced away from the first passageway 40 of the respective first collar 38 in a direction away from the first spillway 34 of the associated insert layer 14. In a similar manner, the lobe 72 on the first dish 56 defines a generally flat surface 74 spaced away from the first containment surface 58 in a direction away from the first spillway 52. The flat surfaces 74 collectively define a stable resting surface for the vessel 10. In embodiments, the first end 18 may be axially aligned with the flat surfaces so as to collectively define a resting surface. In addition, it is preferred that each of the lobes 72 on the second collars 42 defines a generally flat surface 76 spaced away from the second passageway 44 of the respective second collar 42 in a direction away from the second spillway 36 of the associated insert layer 14, and the lobe 72 on the second dish 60 defines a generally flat surface 76 spaced away from the second containment surface 62 in a direction away from the second spillway 54. It is preferred that the flat surfaces 76 be axially aligned with the second end 20 of the lid 12. Individually and collectively, the first end 18 of the lid 12, the first collars 38, and the first dish 56 are protruding supports which collectively define a resting surface for the vessel 10 to be supported in vertical alignment.

Each of the lobes 72 may also include one or more tapered portions 78 to converge from the respective flat surface 74, 76 towards the associate first collar 38, second collar 42, first dish 56 or second dish 60. With the tapered portions 78, the lobes 72 collectively define handling members conveniently-formed to be gripped by a user. With the lobes 72 being at opposite ends of the vessel 10, the vessel 10 may be handled and transported conveniently by a user.

As shown in FIG. 21, the insert layers 14 and/or the base 16 may be provided with one or more protruding support members 80, spaced from the lobes 72. The support members 80 may be truncated so as to define flat surfaces 82 which are disposed to be generally coplanar with the flat surface 74 or the flat surface 76 (depending on which end the support members 80 are located). As disclosed above, individually and collectively, the first end 18, or the apron 18 of the lid 12, the first collars 38, and the first dish 56 are also protruding supports which collectively define a resting surface for the vessel 10 to be supported in vertical alignment.

The vessel 10 may be drained by pouring media from one or both of the first and second ports 22, 24. With the second end 20 being of limited length, it is preferred that the second port 24 be utilized to pour contents from the vessel 10. The limited length of the second end 20 minimizes obstruction, both physical and visual, while pouring. With angled orientation, either the first collective passageway 64 or the second collective passageway 66 will define the gravitational low-point of the enclosed volume of the vessel 10, with the other collective passageway 64, 66 defining the gravitational high-point of the enclosed volume of the vessel 10. This allows for efficient draining and venting. Also, the first and second collective passageways 64, 66 are located to coincide with the longitudinal axis L, which defines not only a center line for the lid 12, but also for the entire vessel 10. This allows for equidistant draining from two halves of the vessel 10 as defined by the longitudinal axis L. Advantageously, the vessel 10 provides equidistant, low-point draining.

Figure 14:
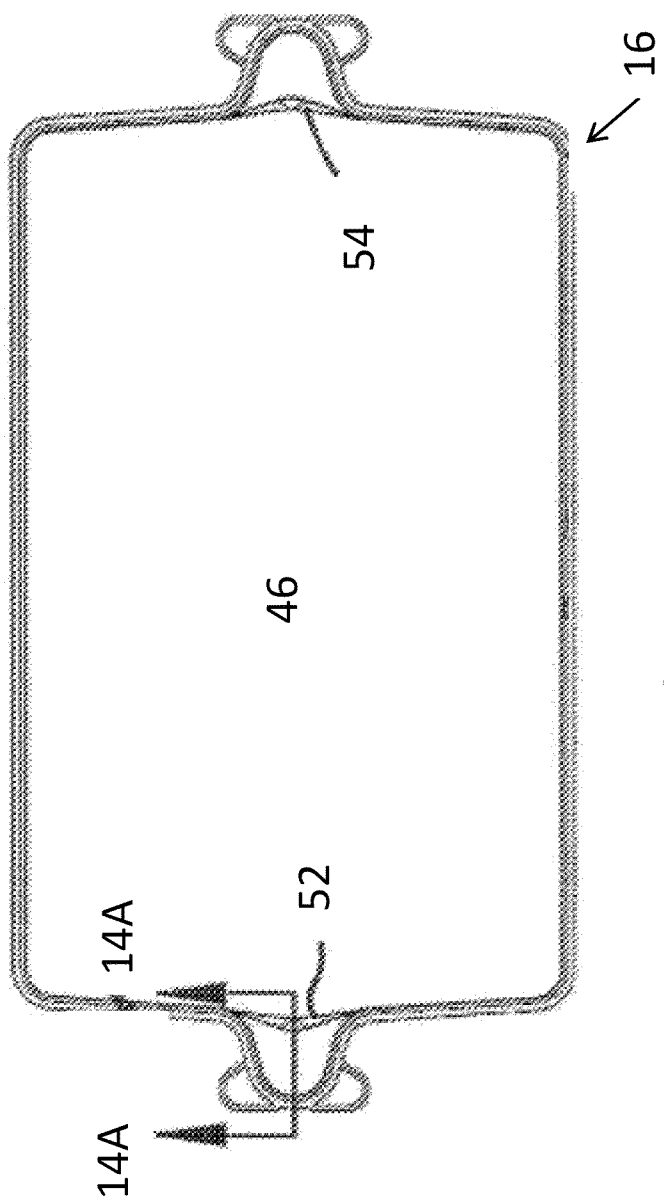
FIG. 14 is a top plan view of a base layer useable in embodiments.
Figure 14A:
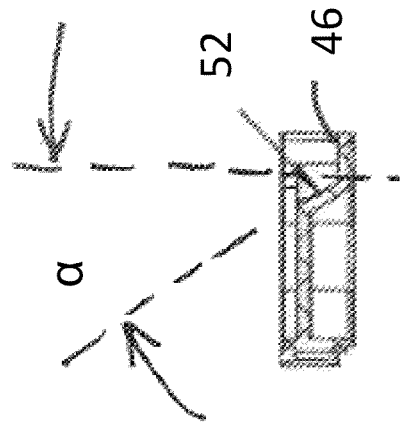
FIG. 14A is a cross-sectional view taken along line 14A-14A of FIG. 14.

Complete drainage is a concern. As shown in FIGS. 14 and 14A, each of the spillways 34, 36, 52, 54 may be formed to bow outwardly to provide a natural edge for pouring media from the insert layers 14 and the base 16. In addition, in embodiments, the spillways 34, 36, 52, 54 are pitched outwardly. In embodiments, the spillways 34, 36, 52, 54 are pitched outwardly an acute angle $\alpha$ relative to a vertical reference axis (disposed perpendicular to the bases 28, 46). This allows for complete drainage of the vessel 10 with orienting the vessel 10 at no more than a 90 degree angle in pouring out its contents. For example, the angle $\alpha$ may be 35 degrees. As such, with the vessel 10 at a 55 degree orientation, the spillways 34, 36, 52, 54 are oriented at 90 degrees. This allows for pouring over the spillways 34, 36, 52, 54 without need for excessive lifting of the vessel 10. To further enhance this effect, for each of the insert layers 14, the portions of the first and second rim portions 30, 32 adjacent the first and second spillways 34, 36 may be convergently angled away from the base 28 so as to create a funneling action towards the respective first or second spillway 34, 36 during a draining process. The first and second rim portions 48, 50 of the base 16 may be similarly configured. As indicated above, it is preferred that the insert layers 14 and the base 16 each define the same footprint.

Figure 16:
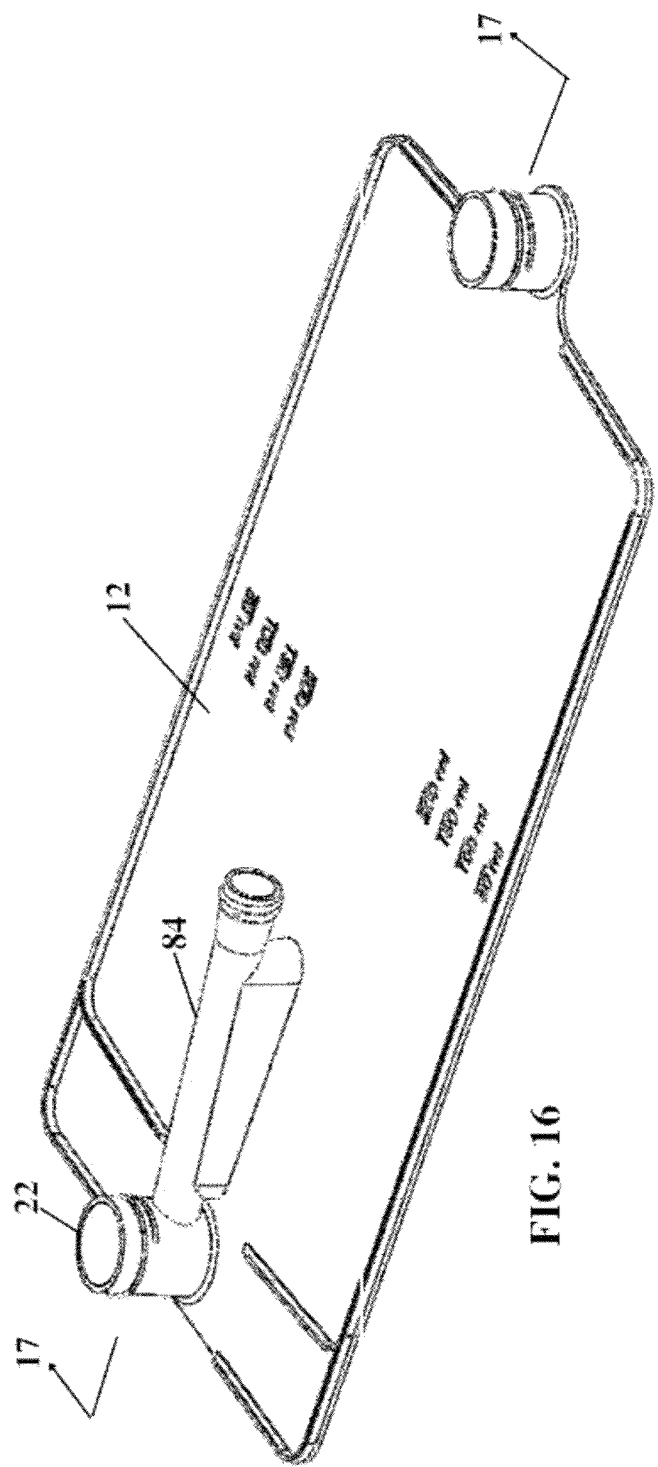
FIG. 16 is an enlarged view of the embodiment of the lid of the disclosed multi-layered flask, showing an optional access port associated with a port.
Figure 17:
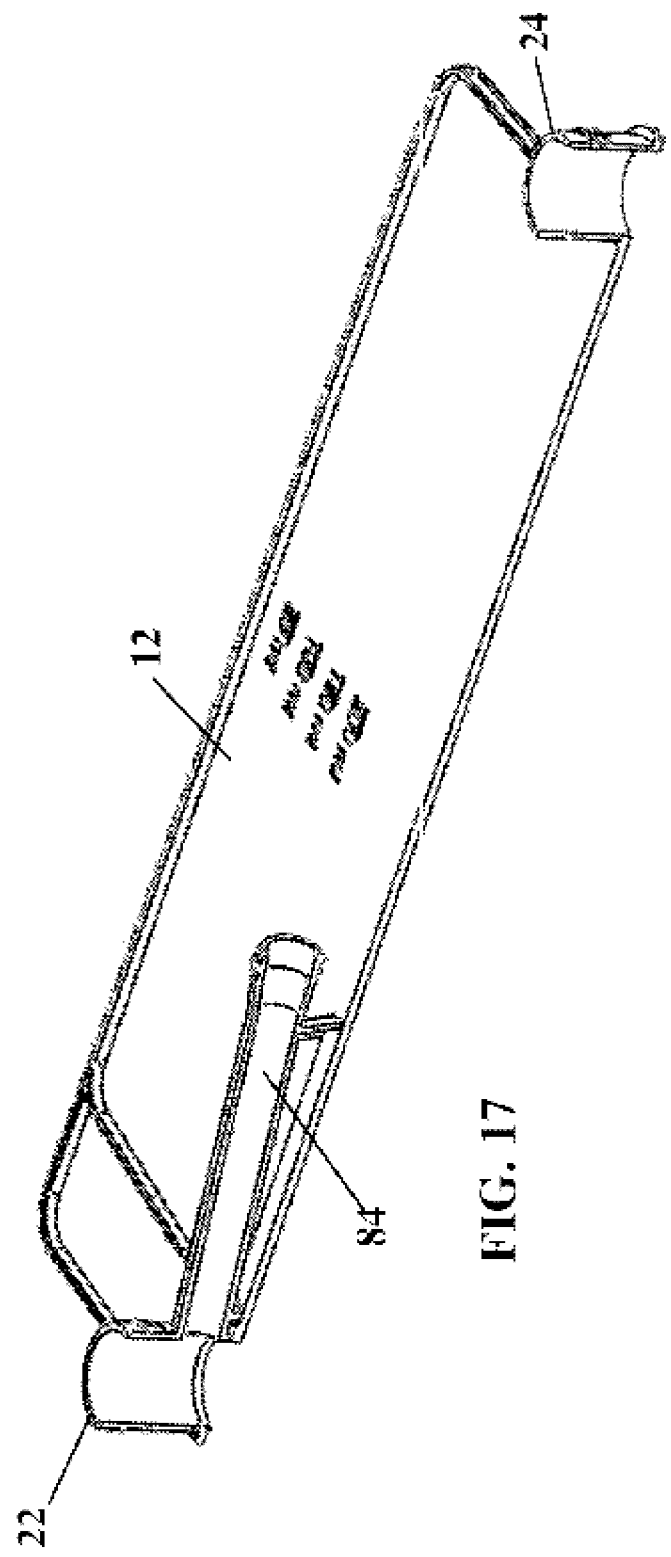
FIG. 17 is a cross-sectional view of the embodiment of the lid of the disclosed multi-layered flask, taken at line 17-17 in FIG. 16.

With reference to FIGS. 15-17, the vessel 10 may be provided with an additional aspiration port 84. Preferably, the aspiration port 84 is in communication with the first port 22. It is preferred that the aspiration port 84 be oriented to be in a vertical position with the vessel 10 resting on the first end 18. The aspiration port 84 permits additional access into the vessel 10 while in vertical alignment. Pipette or other techniques may be used to aspirate cell media from the vessel 10 via the aspiration port 84, particularly, that collected in the first collective passageway 64. The aspiration port 84 may be sealed by a removable cap or closure, as needed. Optionally, the aspiration port 84 may be associated with the second port 24.

Figure 19:
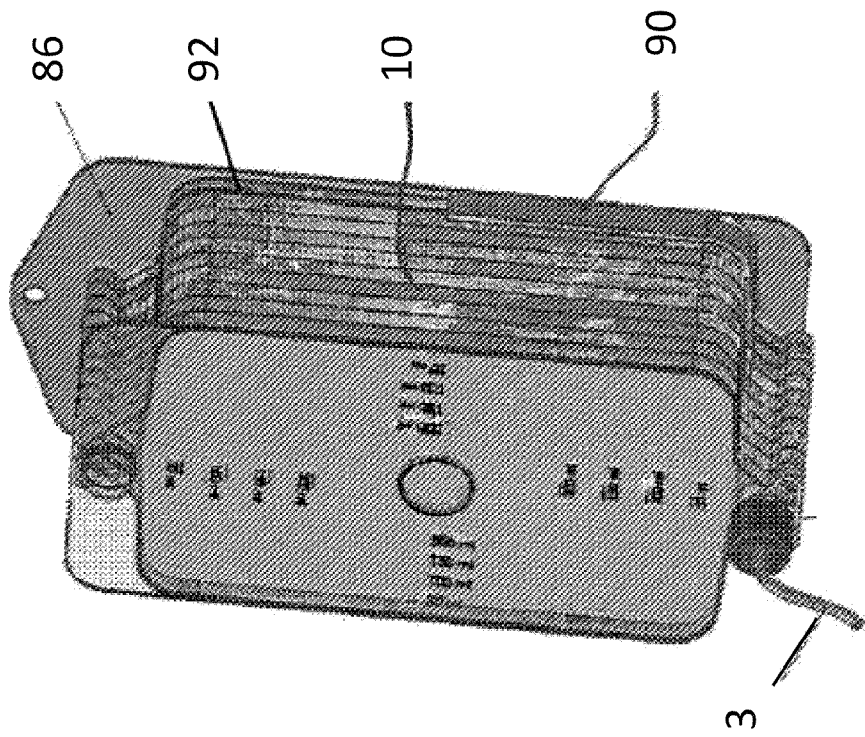
FIG. 19 is a perspective view of an embodiment of the multi-layered flask, engaged into an embodiment of a bracket.
Figure 18:
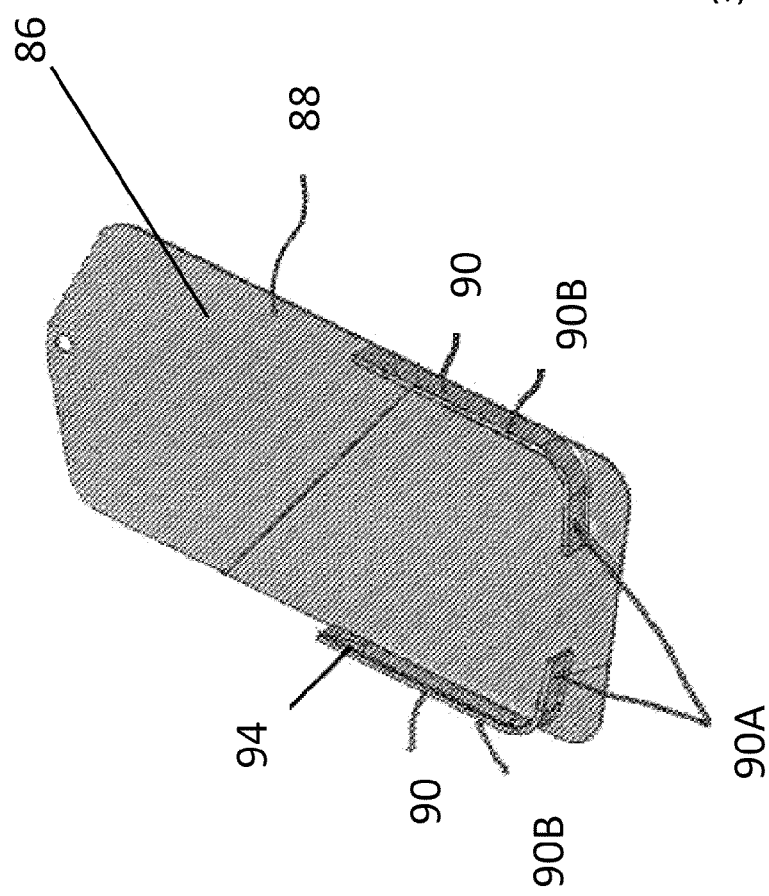
FIG. 18 is a perspective view of an embodiment of a bracket useable with embodiments of the disclosed multi-layered flask.

With reference to FIGS. 18-20, a bracket 86 may be provided configured to support the vessel 10 in a pitched orientation. The bracket 86 includes a planar support 88 with one or more protruding shoulders 90 formed to receive and support the vessel 10. Preferably, the shoulders 90 are formed to provide support both vertically (shoulder portions 90A) and transversely (shoulder portions 90B). The bracket 86 may be wall mounted or supported by another structure. To further enhance the holding force, cooperating elements may be provided on the bracket 86 and the vessel 10. For example, the base 16 may be provided with a protruding lip 92 that is formed to be received within a corresponding channel 94 defined in each of the shoulders 90.

As will be appreciated by those skilled in the art, the vessel 10 provides various advantages such as, for example:

Extending the passageways 64, 66 beyond the general rectangular portion of each layer 14, as shown for example in FIG. 3, and base 16 allows the use of the passageways 64, 66 as handles or grips to improve manual handling of the vessel 10 as described herein. Using the passageways 64, 66 as grips on the vessel improves the user's ability to transport the vessel 10 while maintaining the fluid on each layer because the grips can be used to level the vessel both side-to-side and front-to-back by raising one hand higher than the other and by rotating the bottom plane of the vessel 10 by rolling the user's wrists.

Figure 2:
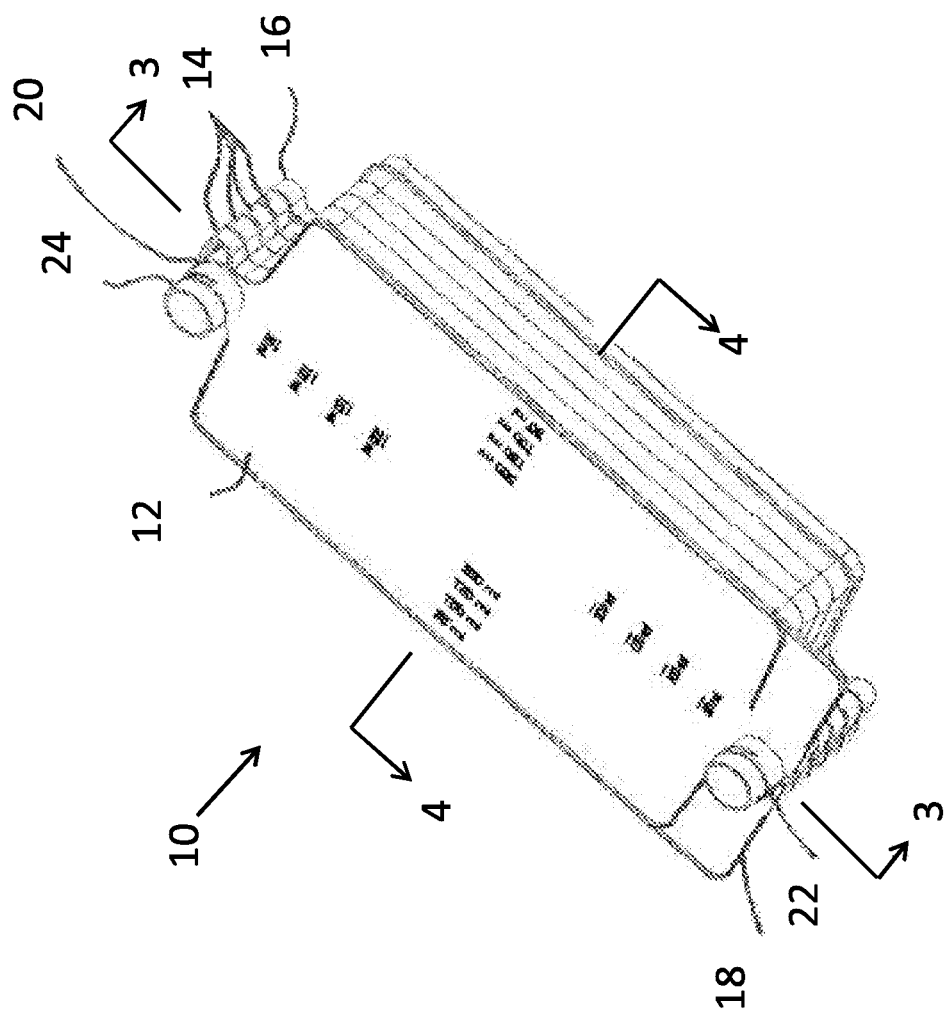
FIG. 2 is a perspective view of the multi-layered cell culture vessel with grips and open ports according to embodiments.

In embodiments, placement of first and second ports 22, 24 (as shown in FIG. 2) along the vessel centerline (L) (shown in FIG. 5) and on opposite ends of the vessel 10 makes the embodiment similar to a pitcher and therefore creates an ergonomically familiar pouring action for the user. In embodiments, extending the second port 24 and second passageway 66 beyond the main body of the vessel provides a feature that looks and performs like the spout on a pitcher. Likewise, by extending the first port 22 and first passageway 64 beyond the main body of the vessel its use as a grip mimics the handle on a pitcher. In this embodiment, the center of mass of the liquid falls directly between the grip established by the first passageway 64 and the second port 24 thereby simplifying the pouring process and improving the user's ability to physically control the pouring process and to complete the pouring process without spilling Placing spillways 34, 36, 52, 54, passageways 64, 66, and ports 22, 24 along the vessel centerline (L) ensures that the vessel 10 is neither right-handed nor left-handed. This enables both right-handed and left-handed users to use the vessel 10 in their preferred workflow method without affecting performance and usage results. Rotating the vessel either clockwise or counterclockwise from the equilibration position is allowed for the partitioning of cells between the layers 14 and base 16.

Placement of first and second ports 22, 24 on opposite ends of the vessel 10 results in one of the ports 22, 24 acting as a venting port at the highest point on the vessel 10 pouring operations. Consequently, venting of the vessel 10 is improved relative to prior art vessels. This configuration virtually ensures that no liquid is poured out of the venting port 22, 24 during pouring and also better enables the smooth flow of liquid from the vessel 10 by allowing the user to fully remove the vent cap (C) from the vessel 10 during pouring to eliminate the creation of a full or partial vacuum in the enclosed volume within the vessel 10. The ports may extend from the top surface of the vessel (as shown in FIG. 2, for example) or, the ports may extend from the end portions of the vessel (not shown).

The end-ported design of the vessel 10 (that is, that the ports are located on each end of the top surface or extending out from an end) lends itself particularly well to the use of a wall mount bracket 86 for closed loop gravity draining of the vessel 10 because the end-ported design allows the ready orientation of vessel so that one port 22, 24 is established as the lowest point on the vessel to act as the drain port and the other port 24, 22 as the highest point on the vessel to act as the vent port.

The design and position of the first and second ports 22, 24 enable the user to easily handle the vessel 10 during an open loop filling process by allowing the user to tilt the vessel 10 up from one end to enable the pouring of liquid down the inside wall of a collective passageway 64, 66 so as to avoid liquid foaming within the vessel 10.

Locating the collective passageways 62, 64 on opposite ends of the vessel 10 minimizes the maximum distance within the vessel 10 to a vent passage (as defined by one or both of the collective passageways 62, 64 to improve gas exchange and minimized gas concentration variations within and between each layer (insert layer 14, base 16). Closer proximity to a vent passage improves gas diffusion and gas exchange.

Locating the passageways 64, 66 on opposite ends of the vessel provides a flow through gas path to improve results during gassing operations. Designing the axis of aspirating port 84 to be along the vessel centerline (L) enables the partitioning of equal fluid volumes among the layers 14 and base 16 of the vessel and ensures that no fluid enters, or is retained in, the aspirating port chamber (internal portion of 84) during the cell culturing process. This in turn ensures that an equal volume of fluid is distributed to each layer 14 and the base 16 and also ensures that fluid cannot leak out of the aspirating port. Designing the axis of the aspirating port 84 to drain back to a passageway 64, 66 ensures that any fluid that enters the aspirating port 84 during processing will drain back to the vessel 10 and to the passageway 64, 66 so that liquid can be equilibrated across each layer of the vessel 10.

Providing angled spillways 34, 36, 52, 54 enables complete fluid aspiration from the vessel 10 through either the first or second port 22, 24 without having to tilt the vessel 10 to a full vertical orientation. This ensures complete aspiration of all fluid from the vessel 10 without fluid spillage. Providing angled spillways 34, 36, 52, 54 enables complete fluid draining from each layer (insert layer 14, base 16) without having to tilt the vessel 10 to or beyond a full vertical orientation.

Providing a specially located and oriented aspiration port 84 allows the user to aspirate the vessel 10 in a hands-free manner without the risk of fluid spillage. Locating the collective passageways 62, 64 offset from the main body of the vessel 10 and using these physical features as grips that are located above the liquid level after the liquid has been evenly distributed among the vessel layers (insert layers 14, base 16) allows for lower risk transport of the vessel 10 while in this even liquid distribution state as compared to currently available vessels. Locating the collective passageways 62, 64 on opposite ends of the vessel 10 allows for rocking of the vessel 10 from one end to the other successive times to homogeneously mix the media and cells within the vessel 10. This feature helps simplify cell culturing operations. Matching the internal radii of the ports 22, 24 and the collective passageways 62, 64 and designing both to share a common centerline minimizes the fluid volume trapped below the port 22, 24 centerlines during gravity draining in the closed loop process and provides the ability to completely drain liquid from the vessel 10 in the open loop pouring process without the need to tilt the vessel 10 beyond a full vertical orientation. Further, the orientation of one collective passageway 64, 66 as the lowest point of the vessel 10 greatly reduces the retained fluid volume within the vessel 10 during draining procedures. In the proposed design, the retained fluid volume is established based on the half cylinder volume of the draining collective passageway 62, 64. Currently available vessel designs retain a fluid volume established by the length and depth of the vessel and the distance from the center of the drain port closure to the side wall. Closed loop gravity draining times when using small gauge tubing (3, see, for example, FIG. 19) is reduced for the proposed design when compared to currently available vessels because the column height of the fluid to be drained from the vessel 10 is higher for the proposed vessel design. For the proposed design, the short end first or second end 18, 20 of the vessel 10 acts as the base of the vessel 10 during draining procedures whereas, with prior art designs, the long side of the vessel longer length side of rectangular shape acts as the base of the vessel during draining. Consequently, the fluid head height is higher for any equivalent liquid volume in the proposed design as compared to currently available vessels. All else being equal (e.g. same tubing gauge, same fluid viscosity, etc.), a greater head height establishes a greater static pressure and the fluid flow rate for draining is increased. As a result, the time to drain the vessel 10 is decreased as compared with prior art designs. Controlled stacking of one vessel 10 atop another is accomplished by the use of molded-in features (e.g., ribs 26 on the lid 12 and bottom 16 of the vessel 10. These features ensure stack integrity while eliminating the need for separate spacers or "stackers" recommended for stacking of prior art vessels. Including a proud lip 92 feature along the exterior of the vessel 10, e.g., at or near its bottom 16, provides a physical feature that will mate with an accessory bracket 86 that can be secured in an elevated location to secure the vessel 10 during closed loop gravity draining. Hanging of a cell culture vessel 10 from a bracket 86 for draining of the vessel 10 in a closed loop operation is made possible by the inclusion of molded-in features (e.g., the lip 92) to the design of the vessel 10.

In embodiments the disclosure provides a multi-layered cell culture vessel having a rectangular shape, an elongated lid extending along a longitudinal axis, said longitudinal axis bisecting said lid, said lid including first and second ports extending therethrough and located spaced apart on said longitudinal axis; at least one insert layer having: a base; a first upstanding rim portion extending from said base; a second upstanding rim portion extending from said base; a first upstanding spillway extending from said base; a second upstanding spillway extending from said base; a first collar extending outwardly from said base adjacent to said first spillway, said first collar defining a first passageway therethrough; and, a second collar extending outwardly from said base adjacent to said second spillway, said second collar defining a second passageway therethrough, wherein, said first and second rim portions extending a first height from said base, said first and second spillways extending from said base less than said first height, said first spillway extending between said first and second rim portions, said second spillway, spaced from said first spillway, extending between said first and second rim portions; and, a bottom having: a first upstanding rim portion extending from said base; a second upstanding rim portion extending from said base; a first upstanding spillway extending from said base; a second upstanding spillway extending from said base; a first dish extending outwardly from said base adjacent to said first spillway; and, a second dish extending outwardly from said base adjacent to said second spillway, wherein, said first and second rim portions extending a first height from said base, said first and second spillways extending from said base less than said first height, said first spillway extending between said first and second rim portions, said second spillway, spaced from said first spillway, extending between said first and second rim portions; wherein, said lid, said at least one insert layer, and said bottom are in stacked arrangement with, said at least one insert layer being located between said lid and said bottom, said first port being in axial alignment with said first passageway of each said insert layer and with said first dish of said bottom, and said second port being in axial alignment with said second passageway of each said insert layer and with said second dish of said bottom.

In a second embodiment the disclosure provides a cell culture vessel as in embodiment 1, wherein a plurality of said insert layers are provided with said first and second rim portions of a lower stacked insert layer being secured to said base of an adjacent, upper stacked insert layer.

In a third embodiment the disclosure provides a cell culture vessel as in embodiment 1, further comprising at least one lobe extending from each said first collar, said at least one lobe defining a generally flat surface spaced from said first passageway in a direction away from said first spillway.

In a fourth embodiment, the disclosure provides a cell culture vessel as in embodiment 3, comprising a cell culture vessel as in claim 3, further comprising at least one lobe extending from each said second collar, said lobe defining a generally flat surface spaced from said second passageway in a direction away from said second spillway.

In a fifth embodiment, the disclosure provides a cell culture vessel as in embodiment 1, wherein said first spillway is pitched outwardly from said base to subtend an acute angle relative to a reference axis perpendicular to said base.

In a sixth embodiment, the disclosure provides a cell culture vessel as in embodiment 5, wherein said second spillway is pitched outwardly from said base to subtend an acute angle relative to a reference axis perpendicular to said base.

In a seventh embodiment, the disclosure provides a cell culture vessel as in embodiment 1, wherein said lid includes first and second ends spaced apart along said longitudinal axis, said first port being located adjacent said first end and said second port located adjacent said second end.

In an eighth embodiment, the disclosure provides a cell culture vessel as in embodiment 3, wherein said lid includes first and second ends spaced apart along said longitudinal axis, said first end being axially aligned with said generally flat surface defined by said at least one lobe so as to define a common resting surface therewith for said cell culture vessel.

In a ninth embodiment, the disclosure provides a multi-layered cell culture vessel comprising: at least two rectangular cell culture compartments having a top, a bottom, two sides and two ends, wherein the sides are longer than the ends, arranged in a stacked orientation with respect to each other; a grip at each end of the cell culture vessel; a port at each end of the cell culture vessel; wherein each port is in fluid communication with each cell culture compartment through a manifold.

In a tenth embodiment, the disclosure provides the multi-layered cell culture vessel of embodiment 9, wherein the grip at each end of the cell culture chamber comprises the port at each end of the cell culture chamber.

In an eleventh embodiment, the disclosure provides the multi-layered cell culture vessel of embodiment 9, wherein at least one of the ports extends beyond the rectangular footprint of the cell culture vessel.

In a twelfth embodiment, the disclosure provides the multi-layered cell culture vessel of embodiment 10 wherein at least one of the ports extends beyond the rectangular footprint of the cell culture vessel.

In a thirteenth embodiment, the disclosure provides the multi-layered cell culture vessel of embodiment 11, wherein the at least one of the ports extends up from the top surface of the rectangular footprint of the cell culture vessel.

In a fourteenth embodiment, the disclosure provides the multi-layered cell culture vessel of embodiment 12, wherein the at least one of the ports extends up from the top surface of the rectangular footprint of the cell culture vessel.

In a fifteenth embodiment, the disclosure provides the multi-layered cell culture vessel of embodiment 11, wherein the at least one of the ports extends out from an end of the rectangular footprint of the cell culture vessel.

In a sixteenth embodiment, the disclosure provides the multi-layered cell culture vessel of embodiment 12, wherein the at least one of the ports extends out from an end of the rectangular footprint of the cell culture vessel.

In a seventeenth embodiment, the disclosure provides the multi-layered cell culture vessel of embodiment 11, wherein a port extends up from the top of the rectangular footprint of the cell culture vessel at each end of the top surface.

In an eighteenth embodiment, the disclosure provides the multi-layered cell culture vessel of embodiment 12, wherein a port extends up from the top of the rectangular footprint of the cell culture vessel at each end of the top surface.

In a nineteenth embodiment, the disclosure provides the multi-layered cell culture vessel of embodiment 9, 10, 11 or 12 wherein the ports at each end of the cell culture vessel are aligned at the midline of the cell culture vessel.

In a twentieth embodiment, the disclosure provides the multi-layered cell culture vessel of embodiment 9, wherein the ports at each end of the cell culture vessel are aligned at the midline of the cell culture vessel.

In a twenty-first embodiment, the disclosure provides the multi-layered cell culture vessel of embodiment 10, wherein the ports at each end of the cell culture vessel are aligned at the midline of the cell culture vessel.

In a twenty-second embodiment, the disclosure provides the multi-layered cell culture vessel of embodiment sixteen, wherein the ports at each end of the cell culture vessel are aligned at the midline of the cell culture vessel.

In a twenty-third embodiment, the disclosure provides the multi-layered cell culture vessel of embodiment 17, wherein the ports at each end of the cell culture vessel are aligned at the midline of the cell culture vessel.

In a twenty-fourth embodiment, the disclosure provides the multi-layered cell culture vessel of embodiment 9, 1 further comprising protruding support members at one end of the cell culture vessel.

In a twenty-fifth embodiment, the disclosure provides the multi-layered cell culture vessel of embodiment 10, further comprising protruding support members at one end of the cell culture vessel.

In a twenty-sixth embodiment, the disclosure provides the multi-layered cell culture vessel of embodiment 9, wherein at least one port further comprises an aspiration port.

In a twenty-seventh embodiment, the disclosure provides the multi-layered cell culture vessel of embodiment 10, wherein at least one port further comprises an aspiration port.

In a twenty-eighth embodiment, the disclosure provides a kit for hanging a multi-layered cell culture vessel on a surface comprising: a multi-layered cell culture vessel comprising least two rectangular cell culture compartments having a top, a bottom, two sides and two ends, wherein the sides are longer than the ends, arranged in a stacked orientation with respect to each other; a hand grip at each end of the cell culture vessel; a port at each end of the cell culture vessel; wherein each port is in fluid communication with each cell culture compartment through a manifold; and, a bracket comprising a planar support and one or more protruding shoulders, structured and arranged to receive the multi-layered cell culture vessel.

In a twenty-ninth embodiment, the disclosure provides the multi-layered cell culture vessel of embodiment 28, wherein the hand grip at each end of the cell culture vessel comprises the port at each end of the cell culture vessel.

In a thirtieth embodiment, the disclosure provides the multi-layered cell culture vessel of embodiment 9 or 19, wherein the fluid flow pathway comprises an angled spillway.

In a thirty-first embodiment, the disclosure provides the multi-layered cell culture vessel of embodiment 10, wherein the fluid flow pathway comprises a spillway.

In a thirty-first embodiment, the disclosure provides the multi-layered cell culture vessel of embodiment 10, wherein the fluid flow pathway comprises an angled spillway.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A multi-layered cell culture vessel comprising:
at least two rectangular cell culture compartments having a lid, a bottom, two sides and two ends, wherein the sides are longer than the ends, arranged in a stacked orientation with respect to each other;
a grip at each end of the cell culture vessel;
a port at each end of the cell culture vessel;
wherein each port is in fluid communication with each cell culture compartment through a fluid flow pathway which allows fluid to flow into each port, through a manifold, and into a cell culture compartment,
wherein the fluid flow pathway comprises an angled spillway.

2. The multi-layered cell culture vessel of claim 1, wherein the grip at each end of the cell culture chamber comprises the port at each end of the cell culture chamber.

3. The multi-layered cell culture vessel of claim 1 wherein at least one of the ports extends beyond the rectangular footprint of the cell culture vessel.

4. The multi-layered cell culture vessel of claim 2 wherein at least one of the ports extends beyond the rectangular footprint of the cell culture vessel.

5. The multi-layered cell culture vessel of claim 3 wherein the at least one of the ports extends up from the top surface of the rectangular footprint of the cell culture vessel.

6. The multi-layered cell culture vessel of claim 4 wherein the at least one of the ports extends up from the top surface of the rectangular footprint of the cell culture vessel.

7. The multi-layered cell culture vessel of claim 3 wherein the at least one of the ports extends out from an end of the rectangular footprint of the cell culture vessel.

8. The multi-layered cell culture vessel of claim 4 wherein the at least one of the ports extends out from an end of the rectangular footprint of the cell culture vessel.

9. The multi-layered cell culture vessel of claim 1 wherein the ports at each end of the cell culture vessel are aligned at the midline of the cell culture vessel.

10. The multi-layered cell culture vessel of claim 2 wherein the ports at each end of the cell culture vessel are aligned at the midline of the cell culture vessel.

11. The multi-layered cell culture vessel of claim 6 wherein the ports at each end of the cell culture vessel are aligned at the midline of the cell culture vessel.

12. The multi-layered cell culture vessel of claim 2 further comprising protruding supports at least one end of the cell culture vessel.

13. The multi-layered cell culture vessel of claim 11 further comprising protruding supports at least one end of the cell culture vessel.

14. The multi-layered cell culture vessel of claim 12 wherein the protruding supports comprise an apron extending from the lid.

15. The multi-layered cell culture vessel of claim 13 wherein the protruding supports comprise an apron extending from the lid.

16. The multi-layered cell culture vessel of claim 1 wherein at least one port further comprises an aspiration port.

17. The multi-layered cell culture vessel of claim 2 wherein at least one port further comprises an aspiration port.

18. A kit for hanging a multi-layered cell culture vessel on a surface comprising:
   a multi-layered cell culture vessel as in claim 1; and,
   a bracket comprising a planar support and one or more protruding shoulders, structured and arranged to receive the multi-layered cell culture vessel.

19. The kit of claim 18 wherein the hand grip at each end of the cell culture vessel comprises the port at each end of the cell culture vessel.

* * * * *